United States Patent
Kitamura et al.

(10) Patent No.: US 10,667,726 B2
(45) Date of Patent: Jun. 2, 2020

(54) GAIT POSTURE METER AND PROGRAM

(71) Applicant: OMRON HEALTHCARE CO., LTD., Muko-shi, Kyoto (JP)

(72) Inventors: Yumi Kitamura, Kyoto (JP); Takeshi Kubo, Kyoto (JP); Yuki Takano, Kyoto (JP)

(73) Assignee: OMRON HEALTHCARE CO., LTD., Kyoto (JP)

(*) Notice: Subject to any disclaimer, the term of this patent is extended or adjusted under 35 U.S.C. 154(b) by 768 days.

(21) Appl. No.: 14/923,734

(22) Filed: Oct. 27, 2015

(65) Prior Publication Data
US 2016/0045140 A1    Feb. 18, 2016

Related U.S. Application Data

(63) Continuation of application No. PCT/JP2014/058909, filed on Mar. 27, 2014.

(30) Foreign Application Priority Data

May 10, 2013 (JP) ................................. 2013-100616

(51) Int. Cl.
*A61B 5/11* (2006.01)
*A61B 5/00* (2006.01)

(52) U.S. Cl.
CPC ............ *A61B 5/112* (2013.01); *A61B 5/1116* (2013.01); *A61B 5/1122* (2013.01);
(Continued)

(58) Field of Classification Search
None
See application file for complete search history.

(56) References Cited

U.S. PATENT DOCUMENTS 9,286,782 B2 * 3/2016 Chang .................. A61B 5/0002
2011/0196264 A1 8/2011 Asada
(Continued)

FOREIGN PATENT DOCUMENTS

JP    2003-204953 A    7/2003
JP    2009-106374 A    5/2009
(Continued)

OTHER PUBLICATIONS

Official Communication issued in International Patent Application No. PCT/JP2014/058909, dated Jun. 17, 2014.

*Primary Examiner* — Sean P Dougherty
*Assistant Examiner* — Benjamin S Melhus
(74) *Attorney, Agent, or Firm* — Keating and Bennett, LLP

(57) ABSTRACT

A gait posture meter that evaluates a gait posture of a measurement subject includes an accelerometer affixed to a centerline of the measurement subject's waist area and a computation unit. The computation unit calculates a Z feature amount and an X feature amount indicating a degree of a difference between up-down and front-rear axis direction accelerations of the waist area in a left leg reference period and up-down and front-rear axis direction accelerations of the waist area in a right leg reference period using a timewise change waveform in three axis accelerations outputted by the accelerometer, and calculates a Y feature amount indicating a degree of a difference between a displacement of a left-right axis direction trajectory of the waist area in the left leg reference period and a displacement of the left-right axis direction trajectory of the waist area in the right leg reference period by finding a second-level integration of the left-right axis acceleration outputted by the accelerometer.

9 Claims, 16 Drawing Sheets

(52) U.S. Cl.
CPC .......... *A61B 5/1128* (2013.01); *A61B 5/6823* (2013.01); *A61B 5/7246* (2013.01); *A61B 5/74* (2013.01); *A61B 2560/0475* (2013.01); *A61B 2562/0219* (2013.01)

(56) References Cited

U.S. PATENT DOCUMENTS

| | | |
|---|---|---|
| 2012/0101771 A1 | 4/2012 | Mori |
| 2013/0090574 A1 | 4/2013 | Kuribayashi et al. |
| 2013/0190658 A1* | 7/2013 | Flaction ............... A61B 5/1038 600/595 |
| 2014/0114453 A1* | 4/2014 | Bentley ................ A61B 5/1122 700/91 |

FOREIGN PATENT DOCUMENTS

| | | |
|---|---|---|
| JP | 2009-261595 A | 11/2009 |
| JP | 2010-119500 A | 6/2010 |
| JP | 2010-268968 A | 12/2010 |
| JP | 2011-78534 A | 4/2011 |
| JP | 2011-251013 A | 12/2011 |

* cited by examiner

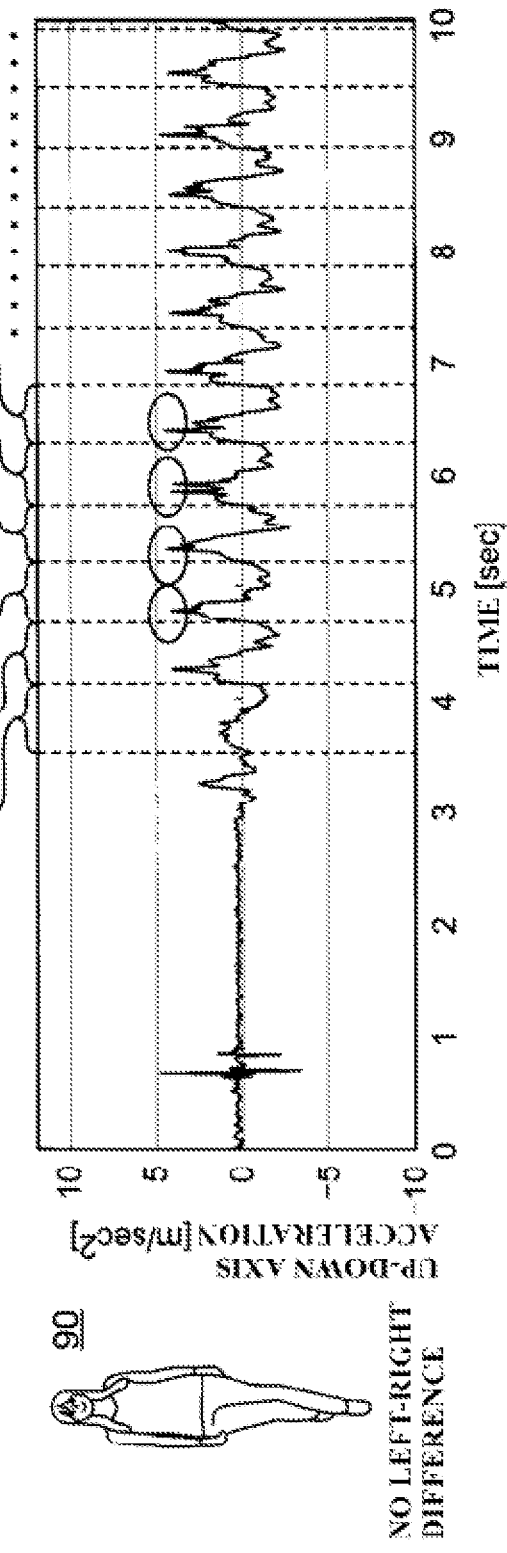
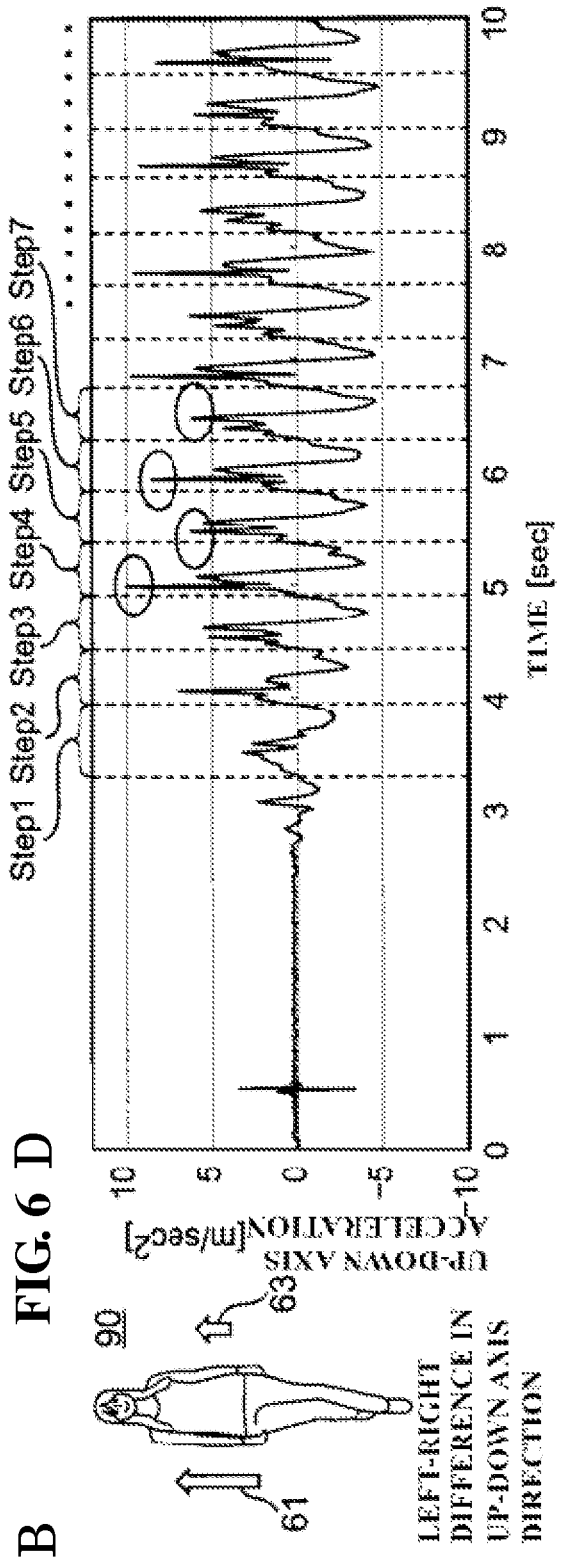

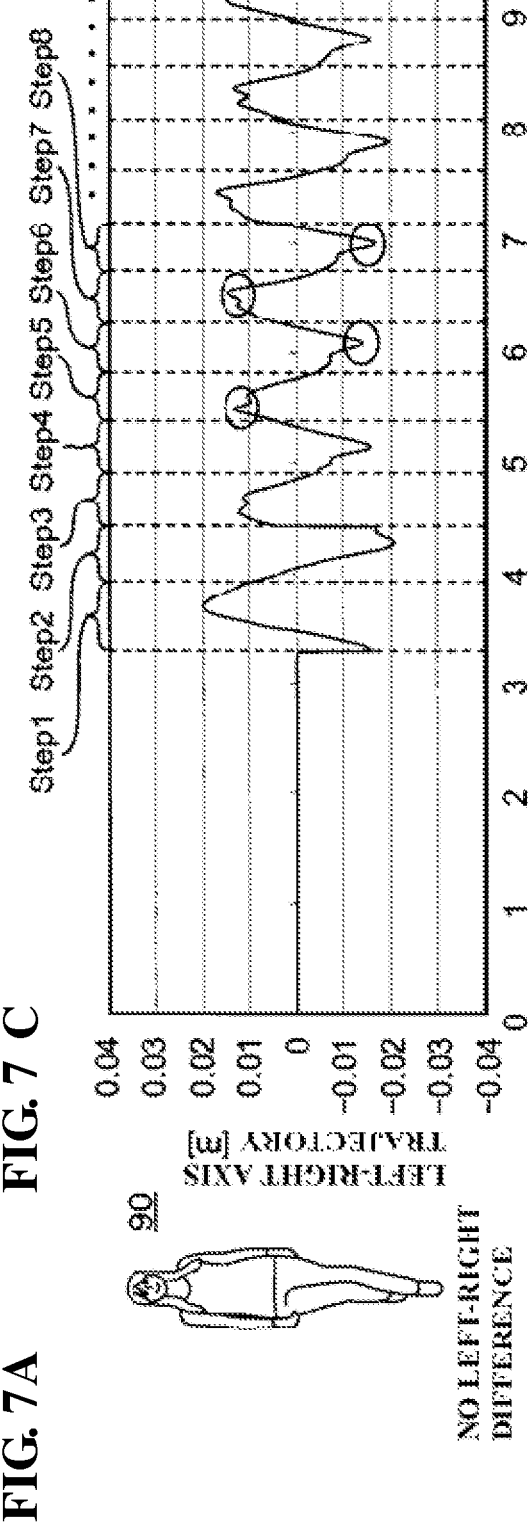
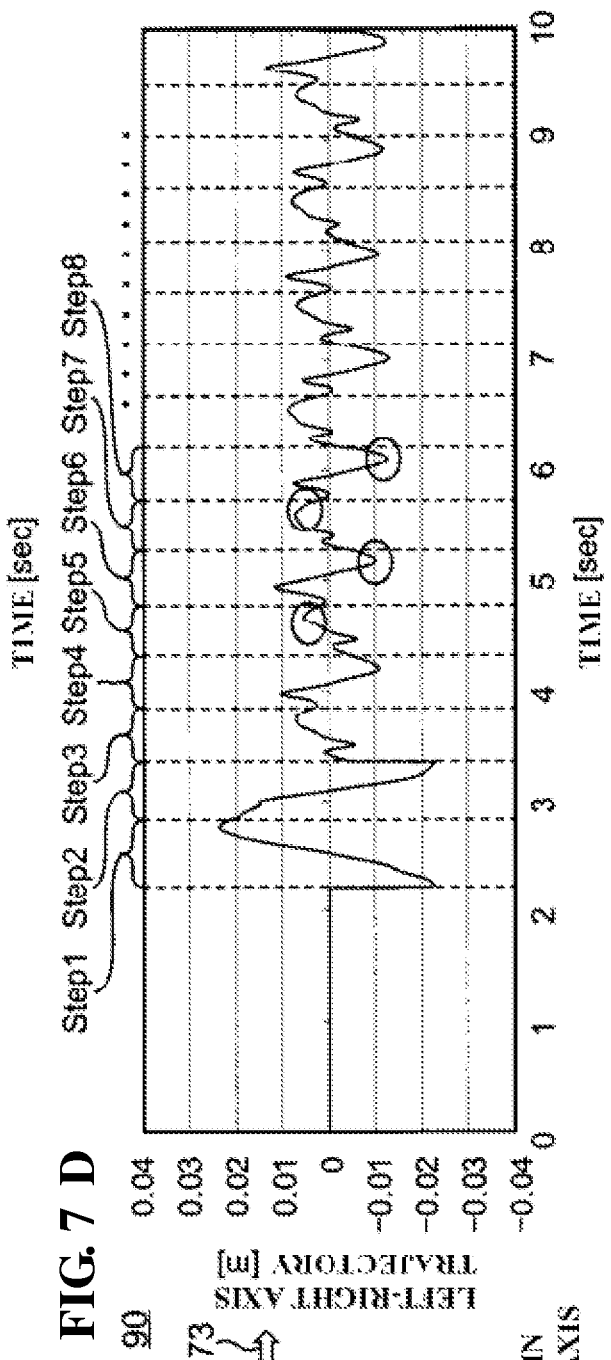
FIG. 7A  FIG. 7C
NO LEFT-RIGHT DIFFERENCE
FIG. 7B  FIG. 7D
LEFT-RIGHT DIFFERENCE IN LEFT-RIGHT AXIS DIRECTION

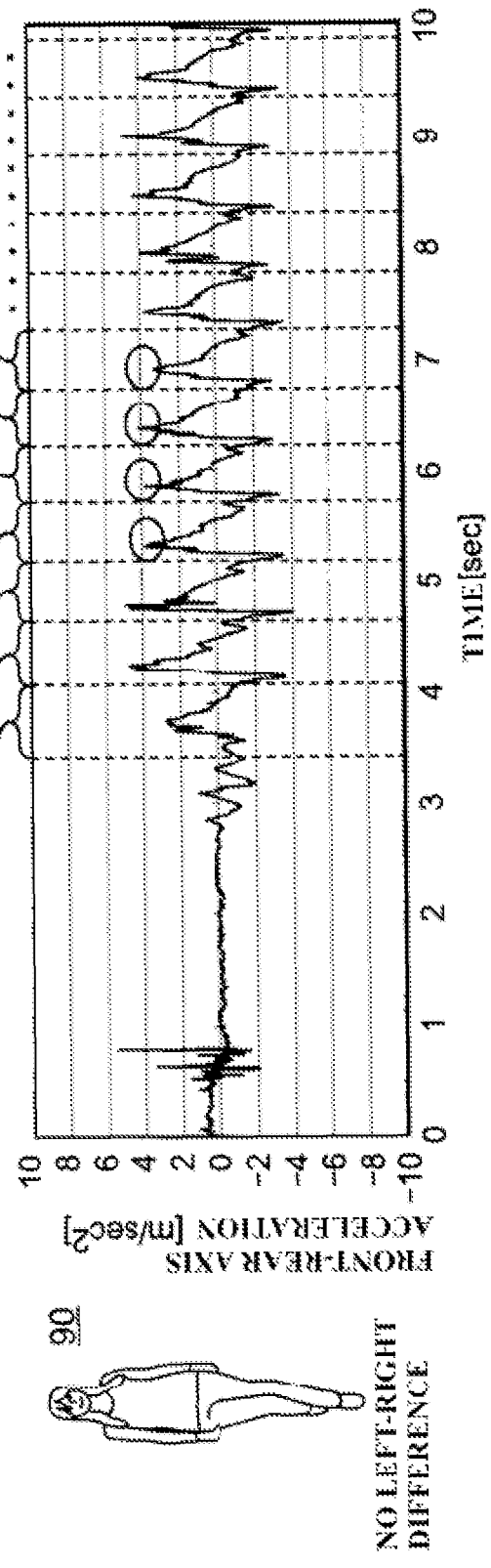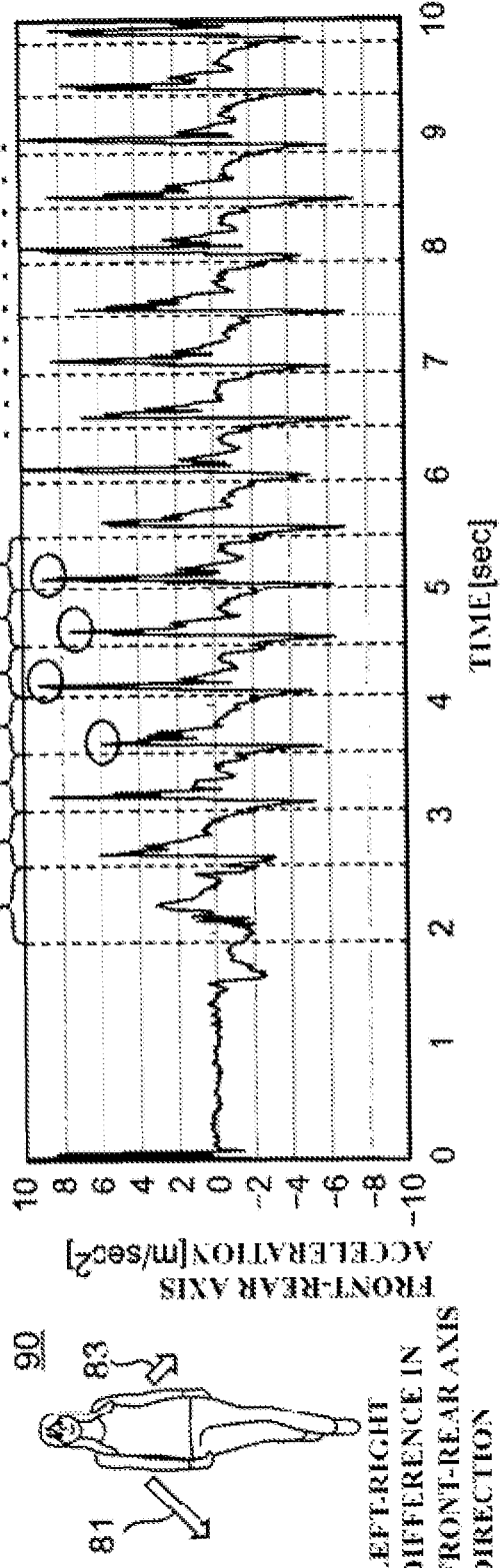

FIG. 14

| | LEFT-RIGHT AXIS SCY | | | | | | | | | | | | UP-DOWN AXIS SCZ | | | | | | | | | | | | FRONT-REAR AXIS SCX | | | | | | | | | | | | CMT |
|---|---|---|---|---|---|---|---|---|---|---|---|---|---|---|---|---|---|---|---|---|---|---|---|---|---|---|---|---|---|---|---|---|---|---|---|---|
| SKEW | 0 | 1 | 2 | 3 | 4 | 5 | 6 | 7 | 8 | 9 | 10 | SKEW | 0 | 1 | 2 | 3 | 4 | 5 | 6 | 7 | 8 | 9 | 10 | SKEW | 0 | 1 | 2 | 3 | 4 | 5 | 6 | 7 | 8 | 9 | 10 | GAIT BALANCE |
| PERSON A | | | | | | | | | | | | PERSON A | | | | | | | | | | | | PERSON A | | | | | | | | | | | | LEFT-RIGHT DIFFERENCE IN UP-DOWN AXIS |
| PERSON B | | | | | | | | | | | | PERSON B | | | | | | | | | | | | PERSON B | | | | | | | | | | | | LEFT-RIGHT DIFFERENCE IN LEFT-RIGHT AXIS |
| PERSON C | | | | | | | | | | | | PERSON C | | | | | | | | | | | | PERSON C | | | | | | | | | | | | LEFT-RIGHT DIFFERENCE IN FRONT-REAR AXIS |
| PERSON D | | | | | | | | | | | | PERSON D | | | | | | | | | | | | PERSON D | | | | | | | | | | | | LEFT-RIGHT DIFFERENCE IN UP-DOWN AXIS, LEFT-RIGHT AXIS, FRONT-REAR AXIS |
| PERSON E | | | | | | | | | | | | PERSON E | | | | | | | | | | | | PERSON E | | | | | | | | | | | | GAIT BALANCE IS GOOD. |

GAIT POSTURE METER AND PROGRAM

BACKGROUND OF THE INVENTION

1. Field of the Invention

This invention relates to gait posture meters, and particularly relates to a gait posture meter that quantitatively evaluates whether or not a person's gait posture is a correct posture.

This invention also relates to a program for causing a computer to execute a method that quantitatively evaluates whether or not a person's gait posture is a correct posture.

2. Description of the Related Art

A body movement balance detection apparatus that detects a left-right balance in the actions of a measurement subject who is moving based on an output, from an accelerometer affixed to the waist area of the measurement subject, related to at least one of a vertical direction acceleration and a left-right direction acceleration of the measurement subject has been proposed as this type of device, as disclosed in JP 2010-119500A for example.

Meanwhile, JP 2010-268968A, for example, discloses a body movement determination apparatus that evaluates whether or not there is imbalance in a person's gait with respect to the left-right direction (a horizontal sideways direction relative to the gait travel direction) based on an output from an accelerometer affixed to the person's trunk area. This apparatus finds a difference between a pitch when the person steps with his/her right foot and a pitch when the person steps with his/her left foot from outputs of the accelerometer regarding a vertical direction acceleration and a left-right direction acceleration, and evaluates the quality of the left-right balance of the person's gait based on the magnitude of the difference between the stated pitches.

In addition, JP 2011-251013A, for example, discloses a mobile electronic device that calculates an up-down axis direction movement amount and a left-right axis direction movement amount of a measurement subject based on outputs from an accelerometer affixed to the measurement subject's waist area and evaluates a measurement subject's gait posture based on those movement amounts.

Furthermore, Matsubara, J., et al, "Gait analysis focusing on gait balance for preventing falls," 70th (2008) National Conference Presentation and Article Collection (4), Information Processing Society of Japan, Mar. 13, 2008, pp. 4-785-4-786, for example, discloses a method for evaluating a left-right difference in the manner in which the center of gravity of a body sways from left-right difference appearing in a plurality of outputs from a plurality of accelerometers affixed to the waist area and both ankles of a measurement subject.

SUMMARY OF THE INVENTION

However, although the stated past apparatuses are capable of determining whether or not there is a left-right difference in motion when walking (a difference between an action when the left leg acts as the supporting leg and an action when the right leg acts as the supporting leg), the apparatuses are not capable of indicating in detail how a breakdown in the left-right balance appears during walking actions.

Accordingly, although a user can know that there is a left-right difference during walking actions, the user cannot know his/her own gait posture and/or what kind of left-right difference is present in his/her walking actions, and has thus been unable to obtain suggestions useful in improving his/her own gait.

Accordingly, an aspect of this invention provides an apparatus capable of more specifically indicating the manner in which a left-right difference appears in a measurement subject's walking actions.

Another aspect of this invention provides computer program capable of more specifically indicating the manner in which a left-right difference appears in a measurement subject's walking actions.

To solve the aforementioned problems, a gait posture meter according to an aspect of the present invention is a gait posture meter that evaluates a gait posture of a measurement subject, and includes an accelerometer that is affixed to a centerline of the measurement subject's waist area and that outputs an acceleration in each of up-down axis, left-right axis, and front-rear axis directions; and a computation unit that calculates a Z feature amount indicating a degree of a difference between an up-down axis acceleration of the waist area in a left leg reference period in which a body is supported by a left leg and an up-down axis acceleration of the waist area in a right leg reference period in which the body is supported by a right leg using a timewise change waveform in the up-down axis acceleration outputted by the accelerometer, calculates a Y feature amount indicating a degree of a difference between a displacement of a left-right axis direction trajectory of the waist area in the left leg reference period and a displacement of the left-right axis direction trajectory of the waist area in the right leg reference period by finding a second-level integration of the left-right axis acceleration outputted by the accelerometer, and calculates an X feature amount indicating a degree of a difference between a front-rear axis acceleration of the waist area in the left leg reference period and a front-rear axis acceleration of the waist area in the right leg reference period using a timewise change waveform in the front-rear axis acceleration outputted by the accelerometer.

In the present specification, "left leg reference period" refers to a period corresponding to a single step of a walking cycle, and particularly refers to a period equivalent to a single step in which the body is supported by the left leg. Specifically, a period spanning from a timing at which the heel of the left foot that has been put forward makes contact with a movement surface to a timing at which the heel of the right foot put forward next makes contact with the movement surface is called the "left leg reference period", for example, although the period is not limited thereto. Likewise, "right leg reference period" refers to a period corresponding to a single step of a walking cycle, and particularly refers to a period equivalent to a single step in which the body is supported by the right leg. Specifically, a period spanning from a timing at which the heel of the right foot that has been put forward makes contact with a movement surface to a timing at which the heel of the left foot put forward next makes contact with the movement surface is called the "right leg reference period", for example, although the period is not limited thereto. Meanwhile, in the present specification, the "left leg reference period" and the "right leg reference period" are referred to simply as "reference periods" in the case where it is not particularly necessary to specify which leg is the supporting leg.

In the present specification, the left-right axis direction trajectory assumes displacement toward the left (a plus side) or toward the right (a minus side) when a gait line along which the measurement subject walks is taken as zero.

In the gait posture meter according to this aspect of the present invention, the accelerometer is affixed to the centerline of the measurement subject's waist area and outputs an acceleration in each of the up-down axis, left-right axis, and front-rear axis directions. The computation unit calculates the Z feature amount indicating the degree of the difference between the up-down axis acceleration of the waist area in the left leg reference period in which a body is supported by the left leg and the up-down axis acceleration of the waist area in the right leg reference period in which the body is supported by the right leg using the timewise change waveform in the up-down axis acceleration outputted by the accelerometer. The computation unit also calculates the Y feature amount indicating the degree of the difference between the displacement of the left-right axis direction trajectory of the waist area in the left leg reference period and the displacement of the left-right axis direction trajectory of the waist area in the right leg reference period by finding a second-level integration of the left-right axis acceleration outputted by the accelerometer. Furthermore, the computation unit calculates the X feature amount indicating the degree of the difference between the front-rear axis acceleration of the waist area in the left leg reference period and the front-rear axis acceleration of the waist area in the right leg reference period using the timewise change waveform in the front-rear axis acceleration outputted by the accelerometer. Accordingly, the degree to which left-right differences appear along each of the three orthogonal axis directions can be indicated in detail based on the Z feature amount, the Y feature amount, and the X feature amount. In particular, the Z feature amount and the X feature amount are each amounts indicating acceleration differences between the left leg reference period and the right leg reference period, and can therefore appropriately indicate a left-right difference in up-down axis direction swaying and a left-right difference in front-rear axis direction swaying, respectively. Meanwhile, the Y feature amount is an amount indicating a difference in the trajectory displacement between the left leg reference period and the right leg reference period, and can therefore appropriately indicate a left-right difference in left-right axis direction swaying.

A gait posture meter according to an embodiment further includes an evaluation unit that compares the Z feature amount to a pre-set first reference and evaluates, in stages, a first difference that is a difference of swaying in the up-down axis direction caused by a disparity in supporting legs, compares the Y feature amount to a pre-set second reference and evaluates, in stages, a second difference that is a difference of swaying in the left-right axis direction caused by a disparity in supporting legs, and compares the X feature amount to a pre-set third reference and evaluates, in stages, a third difference that is a difference of swaying in the front-rear axis direction caused by a disparity in supporting legs.

In the gait posture meter according to this embodiment, the evaluation unit compares the Z feature amount to the pre-set first reference and evaluates, in stages, the first difference that is a difference of swaying in the up-down axis direction caused by a disparity in the supporting legs. In addition, the evaluation unit compares the Y feature amount to the pre-set second reference and evaluates, in stages, the second difference that is a difference of swaying in the left-right axis direction caused by a disparity in supporting legs. Furthermore, the evaluation unit compares the X feature amount to the pre-set third reference and evaluates, in stages, the third difference that is a difference of swaying in the front-rear axis direction caused by a disparity in supporting legs. Accordingly, the first difference expressing the left-right difference in the up-down axis direction swaying, the second difference expressing the left-right difference in the left-right axis direction swaying, and the third difference expressing the left-right difference in the front-rear axis direction can each be indicated in stages.

A gait posture meter according to an embodiment further includes a notification unit that makes a notification of results of the evaluations carried out by the evaluation unit.

With the gait posture meter according to this embodiment, a user can know each of the left-right differences in the swaying of the waist along each of the three orthogonal axis directions in stages.

A gait posture meter according to an embodiment further includes a storage unit that stores a first still image or moving picture indicating a gait posture in which the difference of the swaying in the up-down axis direction caused by the disparity in the supporting legs is greater than the first reference, a second still image or moving picture indicating a gait posture in which the difference of the swaying in the left-right axis direction caused by the disparity in the supporting legs is greater than the second reference, and a third still image or moving picture indicating a gait posture in which the difference of the swaying in the front-rear axis direction caused by the disparity in the supporting legs is greater than the third reference; the notification unit makes a notification that the left-right difference in the up-down swaying of the waist area is high using the first still image or moving picture in the case where the evaluation unit has evaluated the first difference as being greater than the first reference, makes a notification that the left-right difference in the left-right swaying of the waist area is high using the second still image or moving picture in the case where the evaluation unit has evaluated the second difference as being greater than the second reference, and makes a notification that the left-right difference in the front-back swaying of the waist area is high using the third still image or moving picture in the case where the evaluation unit has evaluated the third difference as being greater than the third reference.

With the gait posture meter according to this embodiment, the user can visually know each of the left-right differences in the swaying of the waist along each of the three orthogonal axis directions through images.

In a gait posture meter according to an embodiment, the first still image or moving picture stored in the storage unit includes an image of the gait posture that exaggerates the left-right difference of the up-down swaying of the waist area more than the gait posture in the case where the first difference is approximately the same as the first reference, the second still image or moving picture stored in the storage unit includes an image of the gait posture that exaggerates the left-right difference of the left-right swaying of the waist area more than the gait posture in the case where the second difference is approximately the same as the second reference, and the third still image or moving picture stored in the storage unit includes an image of the gait posture that exaggerates the left-right difference of the front-back swaying of the waist area more than the actual gait posture in the case where the third difference is approximately the same as the third reference.

With the gait posture meter according to this embodiment, the user can visually know each of the left-right differences in the swaying of the waist along each of the three orthogonal axis directions through images in which the left-right difference is exaggerated more than the actual left-right difference. This makes it easier for the user to understand features of the left-right differences in his/her walking.

In a gait posture meter according to an embodiment, the computation unit finds the Z feature amount using an absolute value of a difference between a maximum value of the up-down axis acceleration in the left leg reference period and a maximum value of the up-down axis acceleration in the right leg reference period adjacent to the stated left leg reference period, the computation unit finds the Y feature amount using an absolute value of a difference between a maximum displacement of the left-right axis direction trajectory in the left leg reference period and a maximum displacement of the left-right axis direction trajectory in the right leg reference period adjacent to the stated left leg reference period, and the computation unit finds the X feature amount using an absolute value of a difference between a maximum value of the front-rear axis acceleration in the left leg reference period and a maximum value of the front-rear axis acceleration in the right leg reference period adjacent to the stated left leg reference period.

In the present specification, "maximum displacement of a trajectory" is assumed to be a left-side (plus-side) and right-side (minus-side) absolute value.

With the gait posture meter according to this embodiment, each of the left-right differences in the swaying of the waist along each of the three orthogonal axis directions can be found through extremely simple calculations. Accordingly, the gait posture meter can make quick evaluations with an extremely small level of processing resources.

In a gait posture meter according to an embodiment, for each of four or more sequential left leg reference periods and right leg reference periods that appear in an alternating manner, the computation unit finds the absolute value of the difference between the maximum value of the up-down axis acceleration in the left leg reference period and the maximum value of the up-down axis acceleration in the right leg reference period adjacent to the stated left leg reference period and then finds the Z feature amount using an average value of the plurality of absolute values of the differences that have been found, finds the absolute value of the difference between the maximum displacement of the left-right axis direction trajectory in the left leg reference period and the maximum displacement of the left-right axis direction trajectory in the right leg reference period adjacent to the stated left leg reference period and then finds the Y feature amount using an average value of the plurality of absolute values of the differences that have been found, and finds the absolute value of the difference between the maximum value of the front-rear axis acceleration in the left leg reference period and the maximum value of the front-rear axis acceleration in the right leg reference period adjacent to the stated left leg reference period and then finds the X feature amount using an average value of the plurality of absolute values of the differences that have been found.

With the gait posture meter according to this embodiment, each of the left-right differences in the swaying of the waist along each of the three orthogonal axis directions is found using an acceleration or a movement amount spanning across a plurality of steps. Accordingly, the gait posture meter can make evaluations in a more stable manner.

In a gait posture meter according to an embodiment, the evaluation unit evaluates the left-right difference in the up-down swaying of the waist area over three or more stages using, in addition to the first reference, a plurality of pre-set first sub-references that are different from the first reference, evaluates the left-right difference in the left-right swaying of the waist area over three or more stages using, in addition to the second reference, a plurality of pre-set second sub-references that are different from the second reference, and evaluates the left-right difference in the front-back swaying of the waist area over three or more stages using, in addition to the third reference, a plurality of pre-set third sub-references that are different from the third reference.

With the gait posture meter according to this embodiment, the degree of each of the left-right differences in the swaying of the waist along each of the three orthogonal axis directions is evaluated across three or more stages using an acceleration or a movement amount spanning across a plurality of steps. Accordingly, the user can know the left-right difference in the swaying of his/her waist area along each axis over multiple stages.

In a gait posture meter according to an embodiment, the evaluation unit evaluates the gait posture of the measurement subject as not having a left-right difference in the case where the first difference is less than or equal to the first reference, the second difference is less than or equal to the second reference, and the third difference is less than or equal to the third reference, and the evaluation unit evaluates the gait posture of the measurement subject as having a left-right difference in the case where the first difference is greater than the first reference, the second difference is greater than the second reference, or the third difference is greater than the third reference.

With the gait posture meter according to this embodiment, the gait posture is evaluated as having a left-right difference in the case where there is a left-right difference greater than the reference in the swaying of the waist area along any of the three axes. Accordingly, the user can easily know whether or not there is a left-right difference in his/her walking.

A program according to another aspect of the present invention is a program for causing a computer to execute a method for evaluating a gait posture of a measurement subject, the method including: a step of obtaining an output of an acceleration in each of up-down axis, left-right axis, and front-rear axis directions from an accelerometer that is affixed to a centerline of the measurement subject's waist area; and a step of calculating a Z feature amount indicating a degree of a difference between an up-down axis acceleration of the waist area in a left leg reference period in which a body is supported by a left leg and an up-down axis acceleration of the waist area in a right leg reference period in which the body is supported by a right leg using a timewise change waveform in the up-down axis acceleration outputted by the accelerometer, calculating a Y feature amount indicating a degree of a difference between a displacement of a left-right axis direction trajectory of the waist area in the left leg reference period and a displacement of the left-right axis direction trajectory of the waist area in the right leg reference period by finding a second-level integration of the left-right axis acceleration outputted by the accelerometer, and calculating an X feature amount indicating a degree of a difference between a front-rear axis acceleration of the waist area in the left leg reference period and a front-rear axis acceleration of the waist area in the right leg reference period using a timewise change waveform in the front-rear axis acceleration outputted by the accelerometer.

By executing this program, the computer first obtains the output of the acceleration in each of up-down axis, left-right axis, and front-rear axis directions from the accelerometer that is affixed to the centerline of the measurement subject's waist area. Then, the computer calculates the Z feature amount indicating the degree of the difference between the up-down axis acceleration of the waist area in a left leg reference period in which the body is supported by the left leg and the up-down axis acceleration of the waist area in the right leg reference period in which the body is supported by the right leg using the timewise change waveform in the up-down axis acceleration outputted by the accelerometer, calculates the Y feature amount indicating the degree of the difference between the displacement of the left-right axis direction trajectory of the waist area in the left leg reference period and the displacement of the left-right axis direction trajectory of the waist area in the right leg reference period by finding a second-level integration of the left-right axis acceleration outputted by the accelerometer, and calculates the X feature amount indicating the degree of the difference between the front-rear axis acceleration of the waist area in the left leg reference period and the front-rear axis acceleration of the waist area in the right leg reference period using the timewise change waveform in the front-rear axis acceleration outputted by the accelerometer. Accordingly, the computer can indicate, in detail, the degree to which left-right differences appear along each of the three orthogonal axis directions based on the Z feature amount, the Y feature amount, and the X feature amount. In particular, the Z feature amount and the X feature amount are each amounts indicating acceleration differences between the left leg reference period and the right leg reference period, and can therefore appropriately indicate a left-right difference in up-down axis direction swaying and a left-right difference in front-rear axis direction swaying. Meanwhile, the Y feature amount is an amount indicating a difference in the trajectory displacement between the left leg reference period and the right leg reference period, and can therefore appropriately indicate a left-right difference in left-right axis direction swaying.

As is clear from the foregoing, with the gait posture meter according to an aspect of this invention, what sort of left-right difference appears in the walking actions of a measurement subject can be indicated in detail.

Furthermore, by causing a computer to execute a program according to another aspect of the invention, what sort of left-right difference appears in the walking actions of a measurement subject can be indicated in detail.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 6A is a diagram illustrating an example of a person's walking actions when there is no left-right difference in swaying in an up-down axis direction of the person's body when walking, FIG. 6B illustrates an example of an up-down axis acceleration waveform appearing when the measurement subject illustrated in FIG. 6A is walking, FIG. 6C is a diagram illustrating an example of a person's walking actions when there is a left-right difference in swaying in the up-down axis direction of the person's body when walking, and FIG. 6D illustrates an example of an up-down axis acceleration waveform appearing when the measurement subject illustrated in FIG. 6C is walking.

FIG. 7A is a diagram illustrating an example of a person's walking actions when there is no left-right difference in swaying in a left-right axis direction of the person's body when walking, FIG. 7B illustrates an example of a trajectory waveform for the left-right axis direction appearing when the measurement subject illustrated in FIG. 7A is walking, FIG. 7C is a diagram illustrating an example of a person's walking actions when there is a left-right difference in swaying in the left-right axis direction of the person's body when walking, and FIG. 7D illustrates an example of a trajectory waveform for the left-right axis direction appearing when the measurement subject illustrated in FIG. 7C is walking.

FIG. 8A is a diagram illustrating an example of a person's walking actions when there is no left-right difference in swaying in a front-rear axis direction of the person's body when walking, FIG. 8B illustrates an example of a front-rear axis acceleration waveform appearing when the measurement subject illustrated in FIG. 8A is walking, FIG. 8C is a diagram illustrating an example of a person's walking actions when there is a left-right difference in swaying in the front-rear axis direction of the person's body when walking, and FIG. 8D illustrates an example of a front-rear axis acceleration waveform appearing when the measurement subject illustrated in FIG. 8C is walking.

FIG. 14 is a diagram illustrating an example of three-axis left-right balance evaluation results and comments for a plurality of measurement subjects.

DETAILED DESCRIPTION OF THE PREFERRED EMBODIMENTS

Hereinafter, an embodiment of the invention will be described in detail with reference to the drawings.

Figure 1:
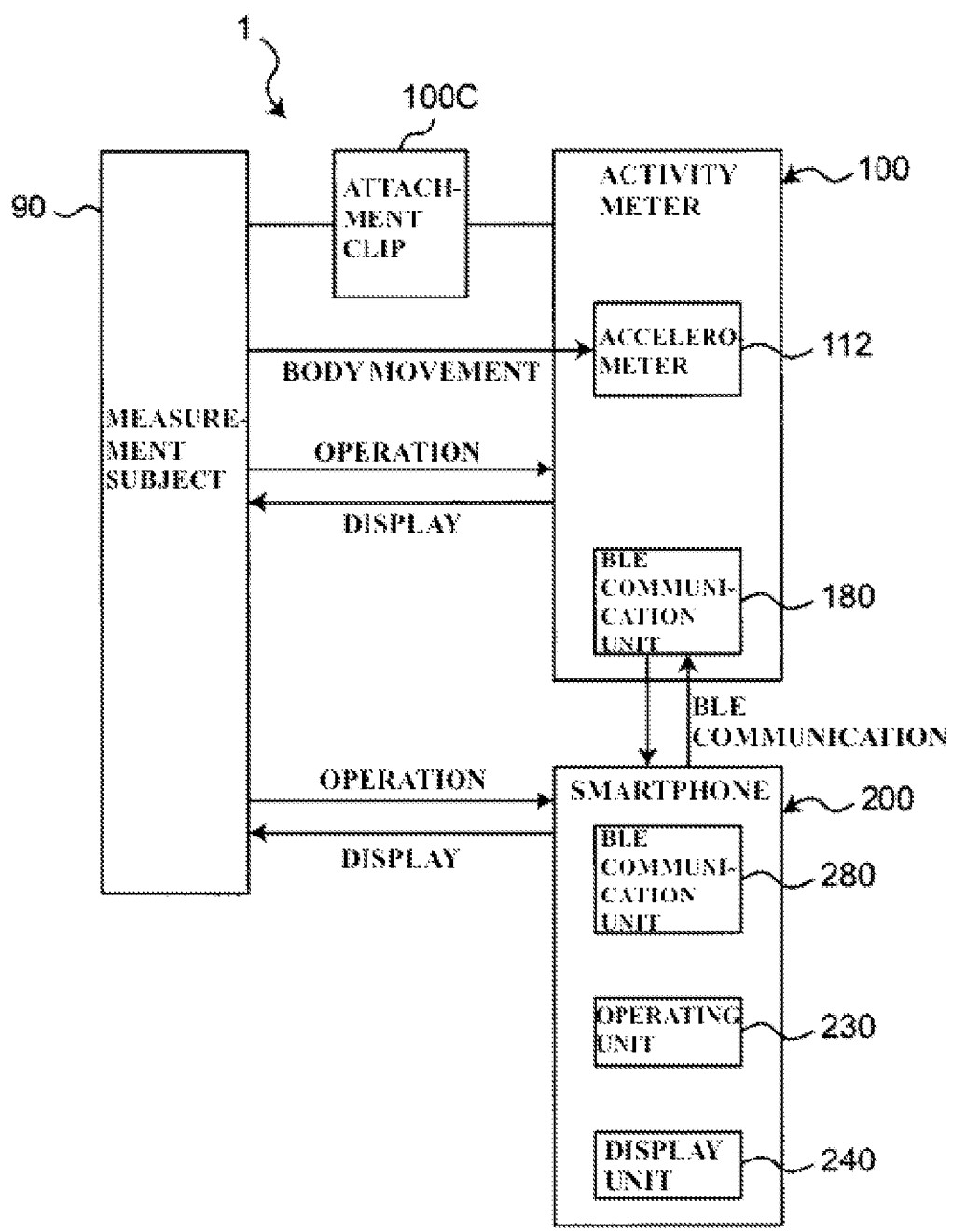
FIG. 1 is a block diagram illustrating a system configuration of a gait posture meter according to an embodiment of this invention.

FIG. 1 illustrates a system configuration of a gait posture meter (generally indicated by reference numeral 1) according to an embodiment of this invention. This gait posture meter 1 includes an activity meter 100 and a smartphone 200. In this example, the activity meter 100 and the smartphone 200 are capable of communicating with each other through BLE (Bluetooth Low Energy, a low-power-consumption Bluetooth defined in Bluetooth Core Specification Ver. 4.0) communication.

Figure 2:
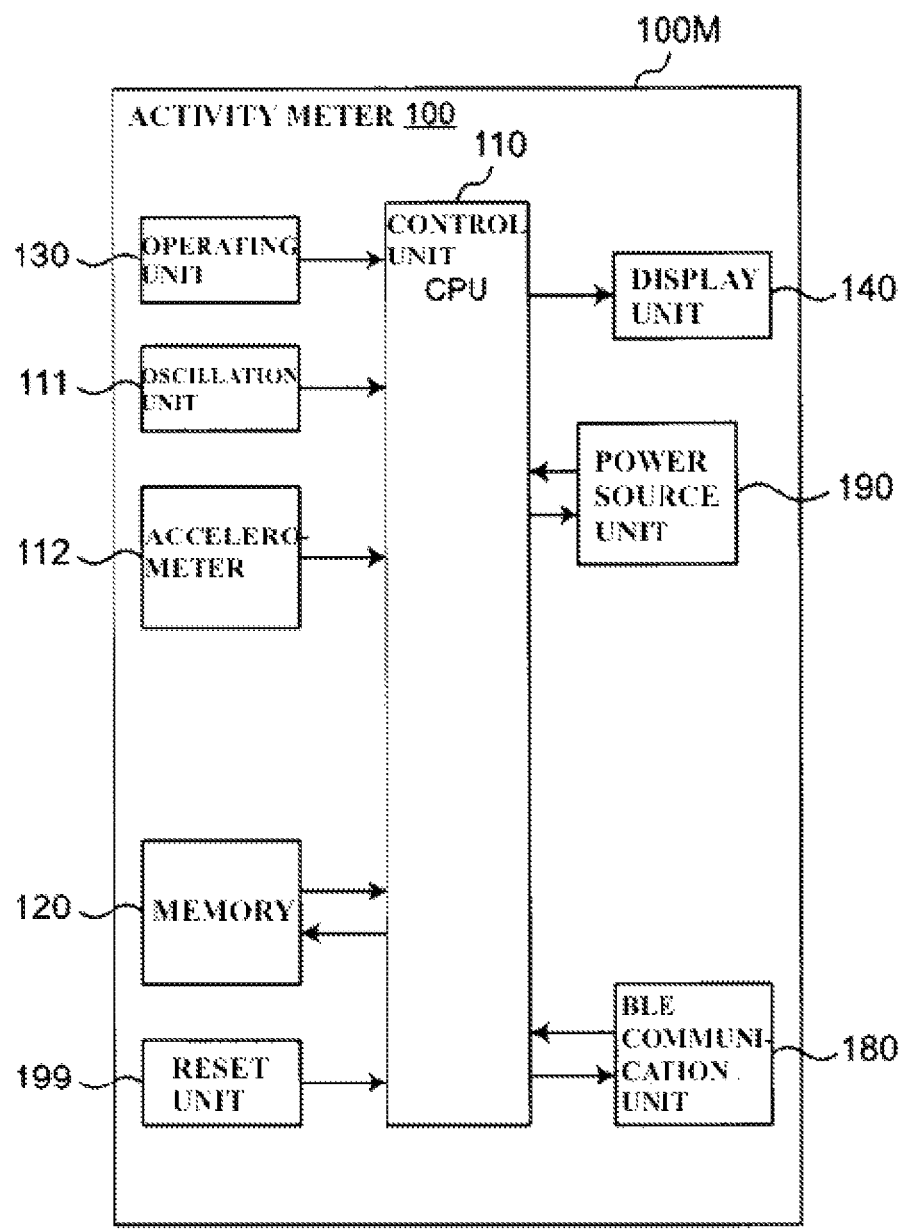
FIG. 2 is a diagram illustrating a block configuration of an activity meter that forms part of the system of the stated gait posture meter.

As illustrated in FIG. 2, the activity meter 100 includes a casing 100M, and a control unit 110, an oscillation unit 111, an accelerometer 112, a memory 120, an operating unit 130, a display unit 140, a BLE communication unit 180, a power source unit 190, and a reset unit 199 provided in the casing 100M.

The casing 100M is formed having a size that fits in the palm of a person's hand so that the activity meter 100 can be carried with ease.

The oscillation unit 111 includes a quartz vibrator, and emits a clock signal that serves as a reference for operational timings in the activity meter 100. The oscillation unit 111 may be a module chip that functions as a clock generator.

The accelerometer 112 detects accelerations in each of three axes (three directions) that the casing 100M is subjected to, and outputs those accelerations to the control unit 110. The accelerometer 112 may be a three-axis accelerometer module chip.

The memory 120 includes a ROM (Read Only Memory) and a RAM (Random Access Memory). The ROM stores data of programs for controlling the activity meter 100. The RAM, meanwhile, stores configuration data for configuring various types of functions of the activity meter 100, acceleration measurement results, data of computational results, and so on. The memory 120 may constitute a storage unit, which will be described in detail below.

The control unit 110 includes a CPU (Central Processing Unit) that operates based on the aforementioned clock signal, and controls the respective units of the activity meter 100 (including the memory 120, the display unit 140, and the BLE communication unit 180) based on detection signals from the accelerometer 112, in accordance with a program for controlling the activity meter 100 stored in the memory 120. The control unit 110 includes a signal processing system capable of processing at least time-series data of an up-down axis acceleration, a left-right axis acceleration, and a front-rear axis acceleration, respectively. The signal processing system generates time-series data of a left-right axis trajectory by processing the time-series data of the left-right axis acceleration, and is also capable of processing the time-series data of the left-right axis trajectory. The control unit 110 functions as a computation unit and an evaluation unit, as will be described in detail below.

The operating unit 130 is in this example constituted of button-based switches, and accepts operational inputs as appropriate, such as operations for switching the power on and off, operations for switching display details, and so on.

The display unit 140 includes a display screen that is in this example configured of an LCD (liquid-crystal display) or an organic EL (electroluminescence) display, and displays predetermined information in the display screen in accordance with signals received from the control unit 110. The display unit 140 may function as a notification unit, which will be described in detail below. The display unit 140 may be an LED (light-emitting diode) that displays whether the power is on or off, operational states, or the like by turning on, turning off, blinking, or the like.

The power source unit 190 is in this example a button battery, and supplies power to the various elements of the activity meter 100.

The BLE communication unit 180 communicates with the smartphone 200 in real time. For example, the BLE communication unit 180 sends information indicating measurement results and the like to the smartphone 200. The BLE communication unit 180 also receives operating instructions from the smartphone 200. The BLE communication unit 180 may be a module chip having a BLE function.

The reset unit 199 is constituted of a switch, and resets and initializes operations of the control unit 110, content stored by the memory 120, and so on.

Figure 3:
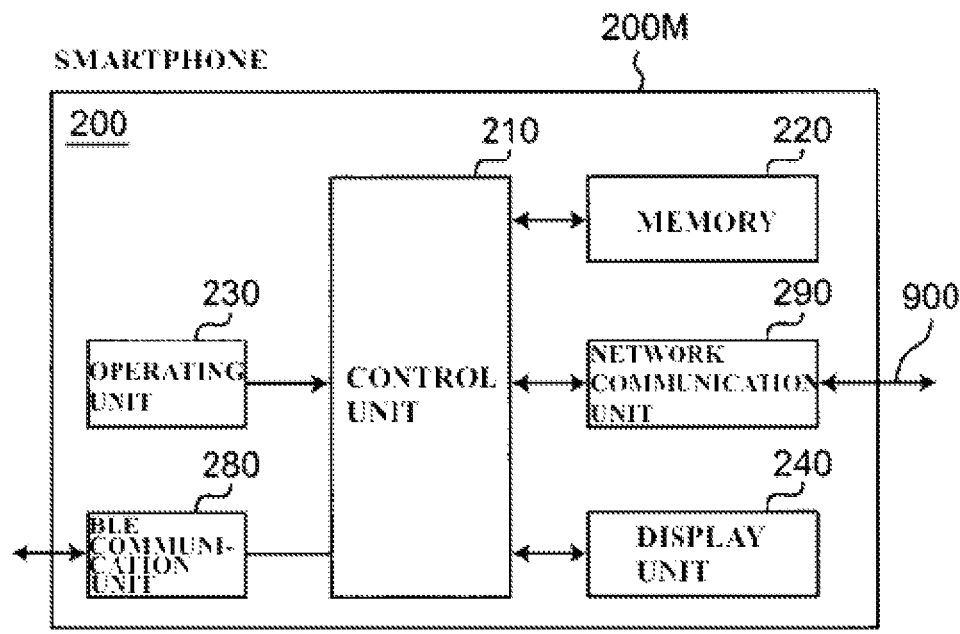
FIG. 3 is a diagram illustrating a block configuration of a smartphone that forms part of the system of the stated gait posture meter.

As illustrated in FIG. 3, the smartphone 200 includes a main body 200M, and a control unit 210, a memory 220, an operating unit 230, a display unit 240, a BLE communication unit 280, and a network communication unit 290 provided in the main body 200M. The smartphone 200 is a commercially-available smartphone in which application software (a computer program) for making instructions to the activity meter 100 has been installed.

The control unit 210 includes a CPU as well as auxiliary circuitry thereof, controls the various units of the smartphone 200, and executes processes in accordance with programs and data stored in the memory 220. In other words, the control unit 210 processes data inputted through the operating unit 230 and the communication units 280 and 290, and stores the processed data in the memory 220, displays the processed data in the display unit 240, outputs the processed data from the communication units 280 and 290, or the like. The control unit 210 may function as a computation unit and an evaluation unit, as will be described in detail below.

The memory 220 includes a RAM used as a work area required by the control unit 210 to execute programs, and a ROM for storing basic programs to be executed by the control unit 210. A semiconductor memory (a memory card, an SSD (Solid State Drive)) or the like may be used as a storage medium in an auxiliary storage unit for complementing a storage region in the memory 220. The memory 220 constitutes a storage unit, which will be described in detail below.

The operating unit 230 is in this example configured of a touch panel provided on the display unit 240. Note, however, that another hardware-based operating device such as a keyboard may be included as well.

The display unit 240 includes a display screen (constituted by, for example, an LCD or an organic EL display). The display unit 240 displays a predetermined image in the display screen under the control of the control unit 210. The display unit 240 constitutes a notification unit, which will be described in detail below.

The BLE communication unit 280 communicates with the activity meter 100 in real time. For example, the BLE communication unit 280 sends operating instructions to the activity meter 100. The BLE communication unit 280 also receives information expressing measurement results and the like from the activity meter 100.

The network communication unit 290 sends information from the control unit 210 to another apparatus over a network 900, and receives information sent over the network 900 from another apparatus and passes the information to the control unit 210.

Figure 4:
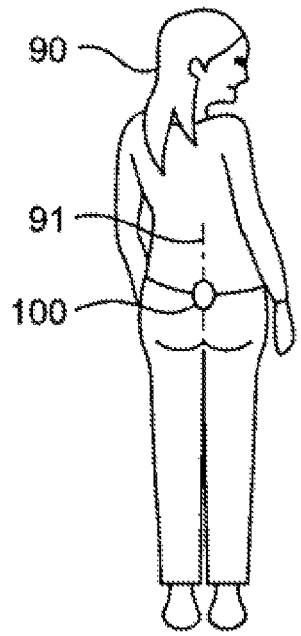
FIG. 4A is a diagram illustrating the activity meter being affixed to a measurement subject.
FIG. 4B is a diagram illustrating an X axis (a front-rear axis), a Y axis (a left-right axis), and a Z axis (an up-down axis).
Figure 4:
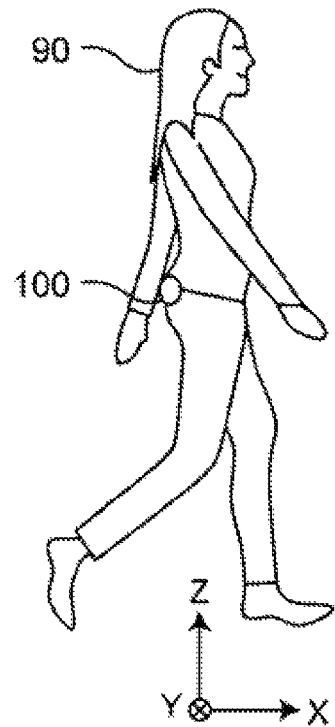

As illustrated in FIG. 4A, in the case where the gait posture meter 1 is used by, for example, a measurement subject 90 serving as a user, the activity meter 100 is affixed at the waist on a rear side of the measurement subject 90, on a centerline 91 thereof, using an attachment clip 100C (indicated in FIG. 1).

In this example, relative to the measurement subject 90, a front-rear direction corresponds to the X axis, a left-right direction corresponds to the Y axis, and an up-down direction corresponds to the Z axis, as illustrated in FIG. 4B. The accelerometer 112 of the activity meter 100 outputs an X axis (front-rear axis) acceleration, a Y axis (left-right axis) acceleration, and a Z axis (up-down axis) acceleration that the casing 100M is subjected to as the measurement subject 90 walks forward.

When a measurement is to be taken using the gait posture meter 1, the measurement subject 90 turns the activity meter 100 and the smartphone 200 on. The measurement subject also launches the application software in the smartphone 200 and instructs the activity meter 100 to start measurement via the operating unit 230 and the BLE communication unit 280.

In this state, the measurement subject 90 walks forward by a predetermined number of steps, which is ten in this example. The measurement subject 90 then instructs the activity meter 100 to perform computation and output a computational result via the operating unit 230 and the BLE communication unit 280 of the smartphone 200.

Upon doing so, the control unit 110 of the activity meter 100 operates as the computation unit, and carries out computations that will be described later. Information expressing the computational result is then sent to the smartphone 200 via the BLE communication unit 180.

Figure 12:
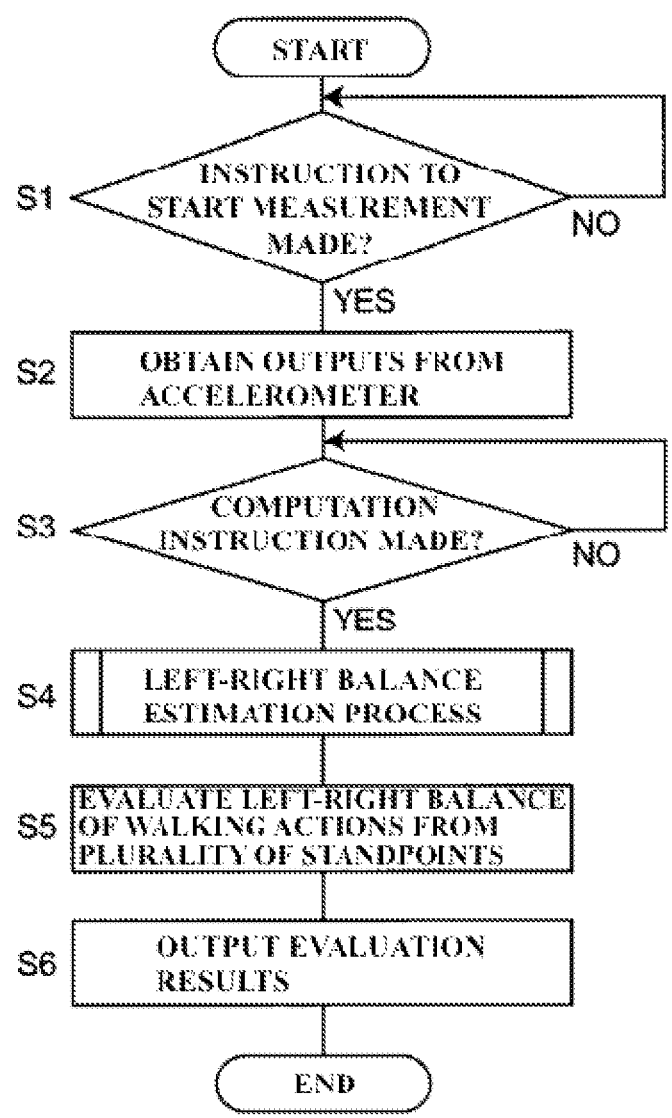
FIG. 12 is a diagram illustrating a flow of operations performed by a control unit of the activity meter.

FIG. 12 illustrates a flow of operations performed by the control unit 110 of the activity meter 100 according to this embodiment. When the power is turned on, the control unit 110 of the activity meter 100 stands by for an instruction from the smartphone 200 to start measurement, as indicated in step S1. Upon receiving an instruction to start measurement from the smartphone 200 (YES in step S1), the control unit 110 obtains a three-axis direction acceleration output from the accelerometer 112, as indicated in step S2. The obtainment of the output from the accelerometer 112 is carried out for a predetermined period (14 seconds, for example), which serves as a period including ten steps' worth of acceleration time-series data in this example. The obtained acceleration time-series data is temporarily stored in the memory 120. Next, the control unit 110 stands by for an instruction to start measurement from the smartphone 200, as indicated in step S3. Upon the instruction for computation from the smartphone 200 being received (YES in step S3), the control unit 110 operates as the computation unit, and as indicated in step S4, calculates a feature amount (a Z feature amount, a Y feature amount, and an X feature amount), indicating the degree of a difference between a left leg reference period and a right leg reference period (a left-right balance (a left-right difference)), for each of the three axis directions of the measurement subject's body (primarily the waist area). Then, as indicated in step S5, the control unit 110 operates as the evaluation unit, and evaluates the left-right balance (left-right difference) in the measurement subject's body while walking using the computational results (the Z feature amount, the Y feature amount, and the X feature amount results) from a plurality of standpoints. Here, the plurality of standpoints refers to a left-right difference in the swaying of the measurement subject's body (primarily the waist area) in the up-down axis direction, a left-right difference in the swaying of the body (primarily the waist area) in the left-right axis direction, and a left-right difference in the swaying of the body (primarily the waist area) in the front-rear axis direction. Then, as indicated in step S6, the results of the evaluations are outputted (sent) to the smartphone 200. Note that the control unit 110 may execute the process of step S4 as soon as at least one step's worth of acceleration time-series data has been obtained. In such a case, the determination step indicated as step S3 may be omitted.

Hereinafter, the process of step S4 in FIG. 12 (a left-right balance estimation process) will be described in detail with reference to FIGS. 5, 6, 7, 8, 9, 10, 11, and 13.

Figure 5:
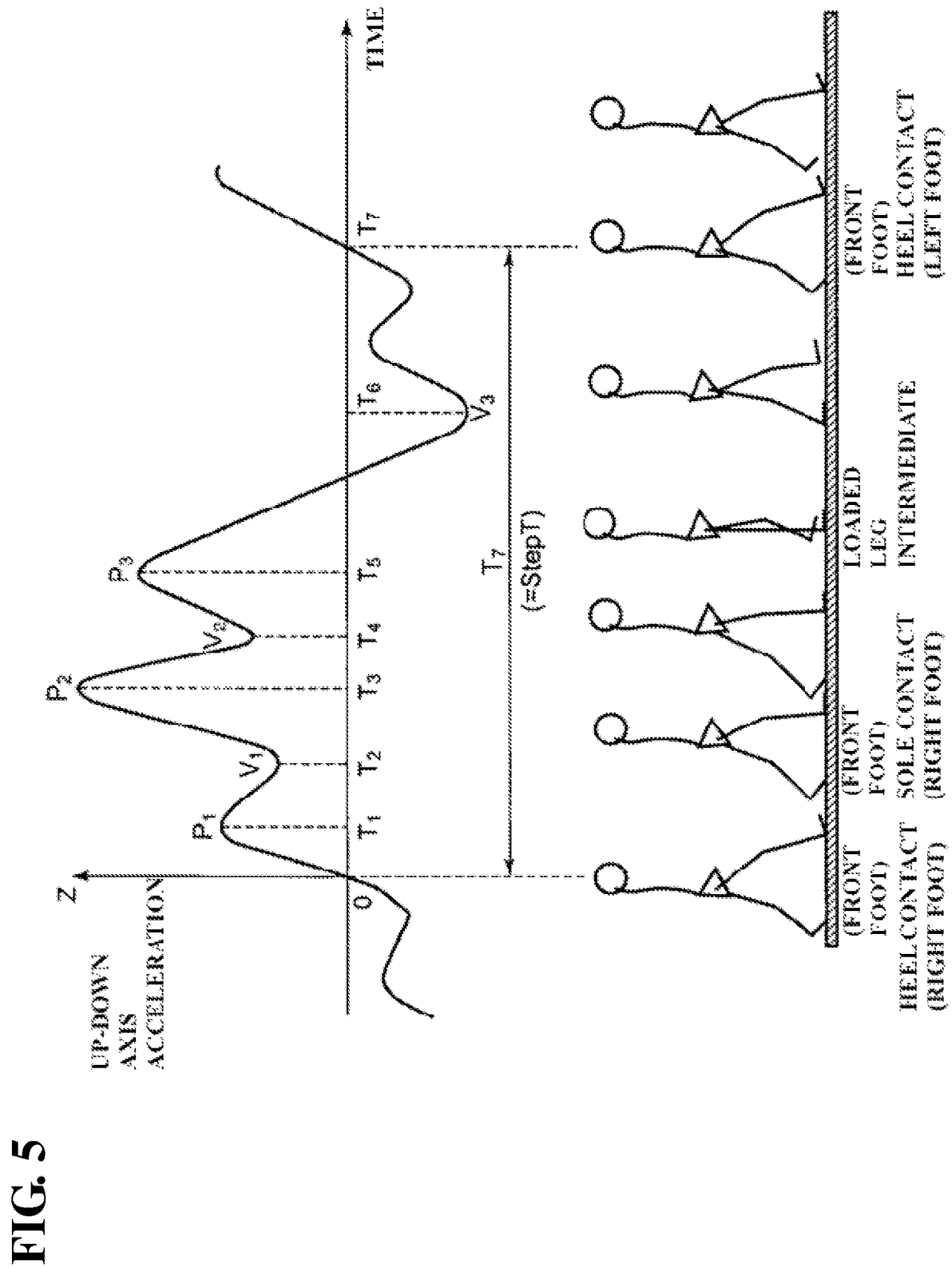
FIG. 5 is a diagram illustrating an example (in the time domain) of an up-down axis acceleration measured by an accelerometer affixed to a person's lower back while the person is walking, and a relationship between a reference period corresponding to one step's worth of a walking cycle and one step's worth of gait.
Figure 9:
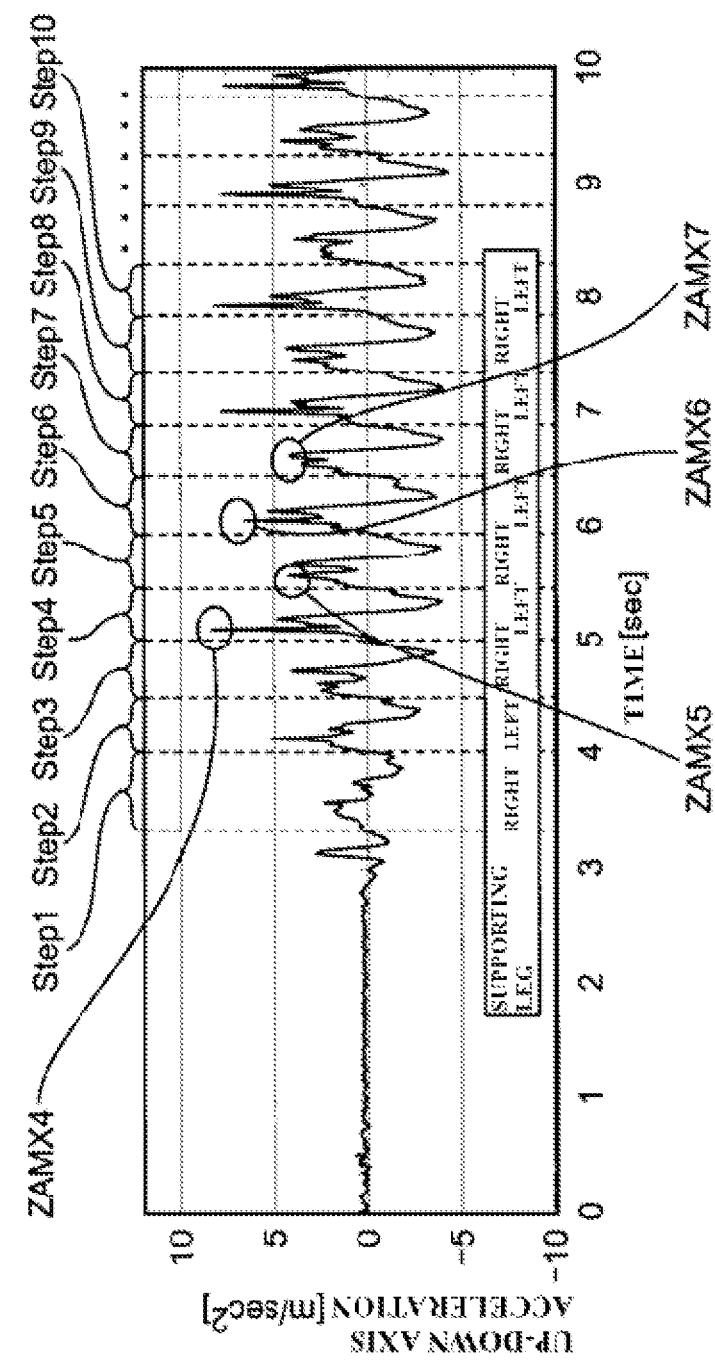
FIG. 9 is a diagram illustrating an up-down axis acceleration time change waveform outputted by an accelerometer.
Figure 10:
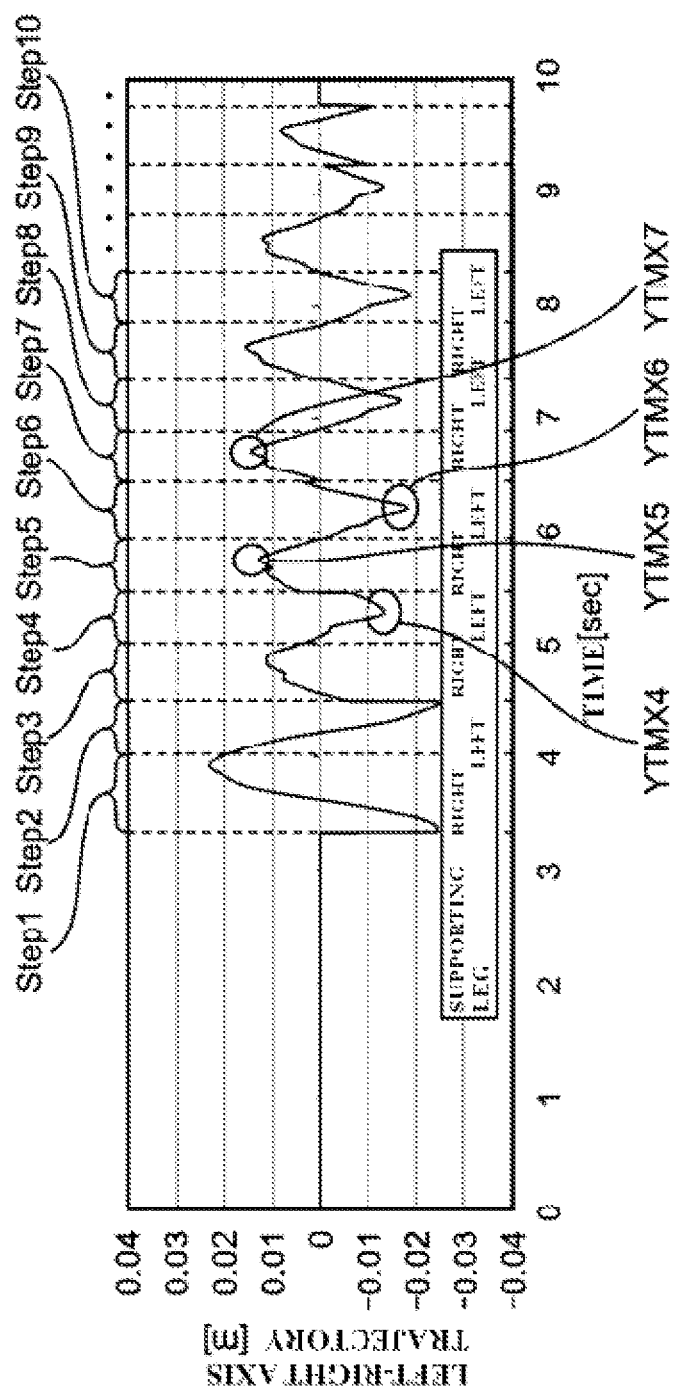
FIG. 10 is a diagram illustrating a left-right axis trajectory time change waveform derived based on a left-right axis acceleration time change waveform outputted by an accelerometer.

FIG. 5 is a diagram illustrating a relationship between a person's gait and a typical example of a time change waveform of the up-down axis acceleration (a Z axis direction acceleration that takes a vertical upward direction as positive) outputted from the accelerometer 112 of the activity meter 100 affixed to the waist during a reference period (T7 in FIG. 5 (=StepT)) that corresponds to one step's worth of a walking cycle.

The up-down axis acceleration passes through a zero crossing point and switches from negative to positive near a timing at which the heel of the front foot (the right foot, in FIG. 5) that has been put out makes contact with a movement surface (a heel contact timing).

Thereafter, three peaks (maximum points) (P1 (time t=T1), P2 (time t=T3), and P3 (time t=T5)), as well as interposing valleys (minimum points) (V1 (time t=T2) and V2 (time t=T4)) appear in the up-down axis acceleration. In the person's gait, a timing at which the loaded leg (the right leg in FIG. 5) and the lifted leg (the left leg in FIG. 5) essentially match with respect to a travel direction (a loaded leg intermediate timing) corresponds to the vicinity of the timing at which the third peak P3 appears.

When, in the person's gait, the loaded leg intermediate timing is passed, the up-down axis acceleration once again passes through the zero crossing point and switches from positive to negative, passes through a minimum point (V3 (time t=T6)), and ultimately passes through the zero crossing point (time t=T7) again at time t=T7 and switches from negative to positive. The zero crossing point at time t=T7 corresponds to the heel contact timing of the next step (in which the left foot is the front foot, in FIG. 5).

In this manner, a waveform appears in the up-down axis acceleration while a person walks one step, as described with reference to FIG. 5. In the present specification, a period (StepT) spanning from the timing at which the heel of the front foot makes contact with the ground (the heel contact timing) to the next heel contact timing is defined as the reference period. Only when is particularly necessary to make a distinction, reference periods for one step by the left foot and one step by the right foot will be distinguished from each other in the following descriptions by referring to a period spanning from the heel contact timing for the left foot to the heel contact timing for the right foot as a left foot reference period and a period spanning from the heel contact timing for the right foot to the heel contact timing for the left foot as a right foot reference period.

In the timewise change waveform of the up-down axis acceleration that takes the upward direction as positive, a period spanning from the timing at which the zero crossing point where the acceleration value changes from negative to positive appears to the timing at which the next zero crossing point where the change from negative to positive appears corresponds to a single reference period.

Next, a relationship between the left-right balance of a person's walking actions and features that appear in the respective waveforms of the three axis accelerations, which became clear through diligent research on the part of the inventors, will be described with reference to FIGS. 6, 7, and 8.

FIGS. 6A to 6D are diagrams illustrating a typical example of up-down axis acceleration (FIG. 6C) of a person having no left-right difference in the swaying of the body in the up-down axis direction (FIG. 6A) and a typical example of up-down axis acceleration (FIG. 6D) of a person having a left-right difference in the swaying of the body in the up-down axis direction (FIG. 6B) when walking. Note that the graphs in FIGS. 6C and 6D indicate the aforementioned heel contact timing as broken lines so that each step can be easily distinguished. In other words, periods Step1, Step2, and so on each correspond to the aforementioned reference period.

In the typical example of up-down axis acceleration (FIG. 6C) of a person having no left-right difference in the swaying of the body in the up-down axis direction (FIG. 6A), no marked difference is apparent in (up-down axis) maximum acceleration values in each reference period (parts enclosed in circles in FIG. 6C, for example).

As opposed to this, in the typical example of up-down axis acceleration (FIG. 6D) of a person having a left-right difference in the swaying of the body in the up-down axis direction (FIG. 6B), a marked difference appears between the (up-down axis) maximum acceleration values in odd-numbered reference periods and the (up-down axis) maximum acceleration values in even-numbered reference periods adjacent thereto. In addition, a relationship between the magnitudes of the (up-down axis) maximum acceleration values in the odd-numbered reference periods (the left leg reference periods or the right leg reference periods) and the (up-down axis) maximum acceleration values in the even-numbered reference periods (the right leg reference periods or the left leg reference periods) adjacent thereto is kept constant in a period containing a plurality of sequential steps. This means that, referring to FIG. 6B, in upward-facing movement of the waist area of the measurement subject 90 while walking, there is a difference in the amount of time required for that movement to reach a maximum velocity. Visually speaking, as indicated in FIG. 6B, in the case of a person whose maximum acceleration 61 in the right leg reference period is greater than a maximum acceleration 63 in the left leg reference period, the left-right difference appears in the movement as the waist area quickly rebounding in the right leg reference period but the waist area gradually moving upward in the left leg reference period. It is thought that the center of gravity of a person who walks in this manner may be skewed to the left or the right. Such a left-right difference in the up-down axis direction body movement is marked in the up-down axis acceleration time change waveform. As such, according to this embodiment of the present invention, the left-right difference in the up-down axis direction swaying of the body during walking is detected from the up-down axis acceleration time change waveform. Through this, the left-right difference in the up-down axis direction swaying of the body during walking can be indicated appropriately. Note that such a left-right difference is not so marked as to appear in an acceleration time change waveform when the time change waveform (velocity and trajectory) has been obtained through a first-level integration or a second-level integration of the up-down axis acceleration.

Next, FIGS. 7A to 7D are diagrams illustrating a typical example of a trajectory waveform in the left-right axis direction (FIG. 7C) of a person having no left-right difference in the swaying of the body in the left-right axis direction (FIG. 7A) and a typical example of a trajectory waveform in the left-right axis direction (FIG. 7D) of a person having a left-right difference in the swaying of the body in the left-right axis direction (FIG. 7B) when walking. Note that the graphs in FIGS. 7C and 7D also indicate the aforementioned heel contact timing as broken lines so that each step can be easily distinguished. In other words, periods Step1, Step2, and so on each correspond to the aforementioned reference period.

In the typical example of a trajectory in the left-right axis direction (FIG. 7C) of a person having no left-right difference in the swaying of the body in the left-right axis direction (FIG. 7A), no marked difference is apparent in the absolute value of a maximum displacement of the left-right axis direction trajectory in each reference period (parts enclosed in circles in FIG. 7C, for example).

As opposed to this, in the typical example of a trajectory waveform in the left-right axis direction (FIG. 7D) of a person having a left-right difference in the swaying of the body in the left-right axis direction (FIG. 7B), a marked difference appears between the absolute values of (left-right axis) maximum displacements in the odd-numbered reference periods and the absolute values of the (left-right axis) maximum displacements in the even-numbered reference periods adjacent thereto. In addition, a relationship between the magnitudes of the absolute values of the (left-right axis) maximum displacements in the odd-numbered reference periods (the left leg reference periods or the right leg reference periods) and the absolute values of the (left-right axis) maximum displacements in the even-numbered reference periods (the right leg reference periods or the left leg reference periods) adjacent thereto is kept constant in a period containing a plurality of sequential steps. This means that, referring to FIG. 7B, there is a difference in left-right direction displacement amounts of the waist area of the measurement subject 90 during walking. Visually speaking, as indicated in FIG. 7B, in the case of a person whose maximum displacement 71 in the right leg reference period is greater than a maximum displacement 73 in the left leg reference period, the left-right difference appears in the movement as the waist area swinging greatly in the right leg reference period but the waist area not swinging as much in the right leg reference period as in the left leg reference period. It is thought that such a left-right difference in the walking actions may appear when there is a left-right difference in the swinging of a person's arms. Such a left-right difference in the left-right axis direction body movement is marked in the left-right axis trajectory time change waveform. As such, according to this embodiment of the present invention, the left-right difference in the left-right axis direction swaying of the body during walking is detected from the left-right axis trajectory time change waveform, which is a second-level integration of the left-right axis acceleration. Through this, the left-right difference in the left-right axis direction swaying of the body during walking can be indicated appropriately.

FIGS. 8A to 8D are diagrams illustrating a typical example of front-rear axis acceleration (FIG. 8C) of a person having no left-right difference in the swaying of the body in the front-rear axis direction (FIG. 8A) and a typical example of front-rear axis acceleration (FIG. 8D) of a person having a left-right difference in the swaying of the body in the front-rear axis direction (FIG. 8B) when walking. Note that the graphs in FIGS. 8C and 8D also indicate the aforementioned heel contact timing as broken lines so that each step can be easily distinguished. In other words, periods Step1, Step2, and so on each correspond to the aforementioned reference period.

In the typical example of front-rear axis acceleration (FIG. 8C) of a person having no left-right difference in the swaying of the body in the front-rear axis direction (FIG. 8A), no marked difference is apparent in (front-rear axis) maximum acceleration values (parts enclosed in circles in FIG. 8C, for example) in each reference period.

As opposed to this, in the typical example of front-rear axis acceleration (FIG. 8D) of a person having a left-right difference in the swaying of the body in the front-rear axis direction (FIG. 8B), a marked difference appears between the (front-rear axis) maximum acceleration values in odd-numbered reference periods and the (front-rear axis) maximum acceleration values in even-numbered reference periods adjacent thereto. In addition, a relationship between the magnitudes of the (front-rear axis) maximum acceleration values in the odd-numbered reference periods (the left leg reference periods or the right leg reference periods) and the (front-rear axis) maximum acceleration values in the even-numbered reference periods (the right leg reference periods or the left leg reference periods) adjacent thereto is kept constant in a period containing a plurality of sequential steps. This means that, referring to FIG. 8B, there is a difference in a forward-facing movement of the waist area of the measurement subject 90 during walking. Visually speaking, as indicated in FIG. 8B, in the case of a person whose maximum acceleration 81 in the right leg reference period is greater than a maximum acceleration 83 in the left leg reference period, the left-right difference appears in the movement as the foot moving extensively inward (a direction that crosses a center axis of the travel direction) in the right leg reference period but the foot not moving as far inward in the left leg reference period as in the right leg reference period. It is thought that the orientation of the pelvis of a person who walks in such a manner may not be staying at a right angle relative to the travel direction. Such a left-right difference in the front-rear axis direction body movement is marked in the front-rear axis acceleration time change waveform. As such, according to this embodiment of the present invention, the left-right difference in the front-rear axis direction swaying of the body during walking is detected from the front-rear axis acceleration time change waveform. Through this, the left-right difference in the front-rear axis direction swaying of the body during walking can be indicated appropriately. Note that such a left-right difference is not so marked as to appear in an acceleration time change waveform when the time change waveform (velocity and trajectory) has been obtained through a first-level integration or a second-level integration of the front-rear axis acceleration.

Next, the process of step S4 in FIG. 12 (the left-right balance estimation process) will be described in detail with reference to FIGS. 9, 10, 11, and 13.

Figure 13:
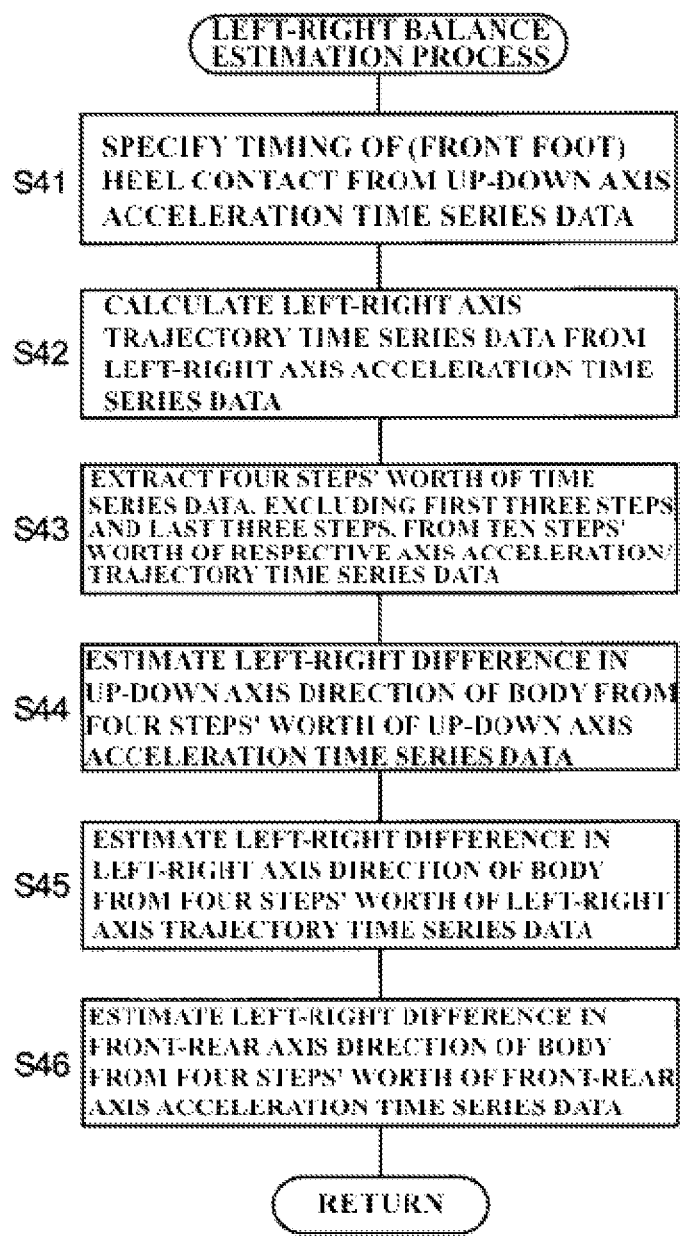
FIG. 13 is a diagram illustrating a flow of a left-right balance estimation process performed by the control unit of the activity meter.

Referring to FIG. 13, in the left-right balance estimation process, the control unit 110 generates up-down axis acceleration time-series data from the three axis acceleration time change waveforms obtained in step S2, detects a timing of the zero crossing point where the movement switches from negative to positive (a time t=0 in FIG. 5) from the generated up-down axis acceleration time-series data, and specifies the timing that has been detected (based on the experimental evidence indicating that the zero crossing point essentially matches the heel contact timing) as the heel contact timing. The control unit 110 detects the next zero crossing point where the movement switches from negative to positive in the same manner, and specifies that timing as the start of the reference period for the next step (as the end of the current reference period) (step S41). In this manner, the control unit 110 specifies at least ten continuous steps' worth of reference periods (Step1 to Step10 in FIG. 9).

Next, in step S42, the control unit 110 calculates left-right axis trajectory time-series data (FIG. 10) from the left-right axis acceleration time-series data.

Figure 11:
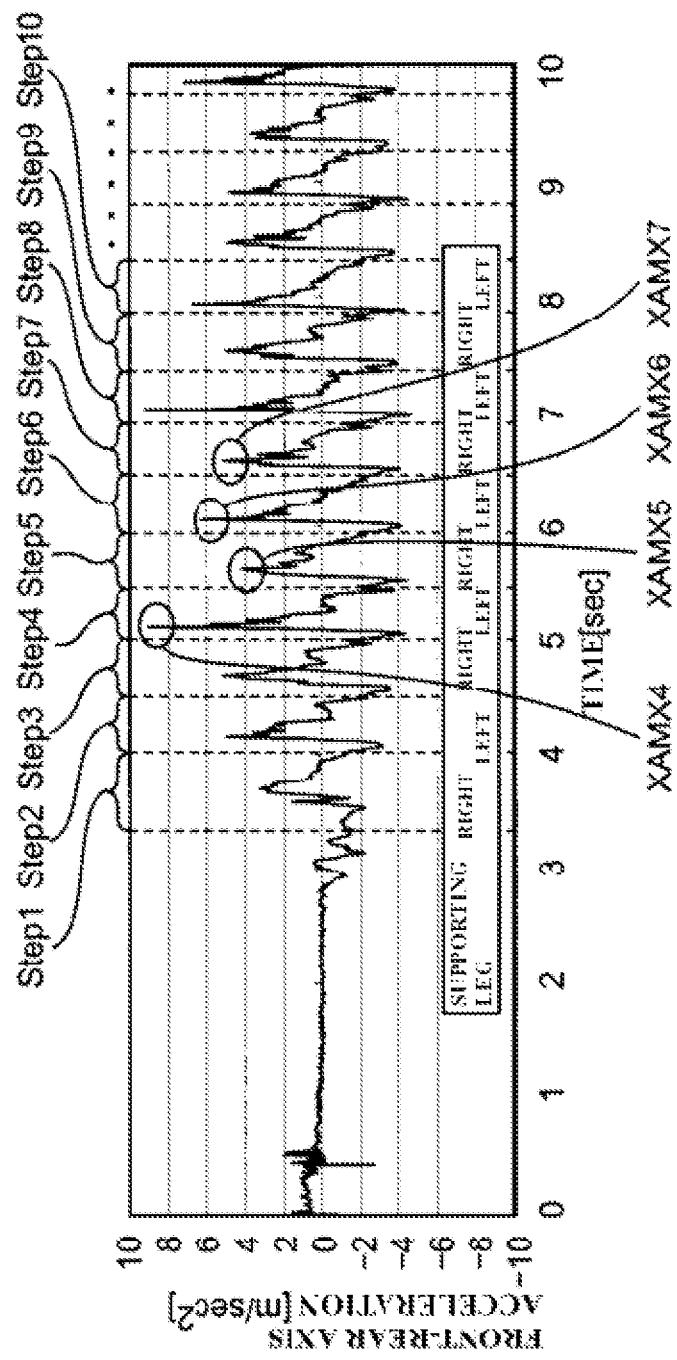
FIG. 11 is a diagram illustrating a front-rear axis acceleration time change waveform outputted by an accelerometer.

Next, in step S43, the control unit 110 extracts four steps' worth (Step4 to Step7) of time-series data, excluding the first three steps (Step1 to Step3) and the last three steps (Step8 to Step10), from the ten steps' worth (Step1 to Step10) of data from the measurement starts of each of the up-down axis acceleration time-series data (FIG. 9), the left-right axis trajectory time-series data (FIG. 10), and front-rear axis acceleration time-series data (FIG. 11). This process has an effect of ensuring that disturbances in the gait posture near a measurement starting time and ending time do not affect the evaluation results. The time-series data spanning the reference periods of the four sequential steps extracted in this manner is used in the process of step S44, the process of step S45, and the process of step S46.

In step S44, the control unit 110 calculates an amount (the Z feature amount) indicating a degree of a difference between the swaying of the body (primarily the waist area) in the up-down axis direction in the left leg reference period and the swaying of the body (primarily the waist area) in the up-down axis direction in the right leg reference period, using the four steps' worth of up-down axis acceleration time-series data.

Specifically, in step S44, the control unit 110 calculates an absolute value of a difference between a maximum value of the up-down axis acceleration in a given left leg reference period contained in the four step's worth of up-down axis acceleration time-series data (for example, an even-numbered reference period) and a maximum value of the up-down axis acceleration in a right leg reference period (an odd-numbered reference period) adjacent to the stated left leg reference period, and takes the calculated absolute value as the Z feature amount. For example, referring to FIG. 9, assuming an up-down axis acceleration maximum value in a reference period Step$i$ (where i is 4 to 7) is represented by ZAMX$i$, the Z feature amount is an amount indicated as follows:

$$Z \text{ feature amount} = |ZAMX6 - ZAMX7| \quad (1a)$$

Or:

$$Z \text{ feature amount} = |ZAMX5 - ZAMX6| \quad (1b)$$

Note that the control unit 110 may find a plurality of absolute values of the difference between the maximum value of the up-down axis acceleration in the left leg reference period and the maximum value of the up-down axis acceleration in the right leg reference period adjacent to that left leg reference period for the four step's worth of up-down axis acceleration time-series data, and may use an average value of the plurality of the absolute values of the differences found in this manner as the Z feature amount. In this case, referring to FIG. 9, $$Z \text{ feature amount} = (|ZAMX4 - ZAMX5| + |ZAMX5 - ZAMX6| + |ZAMX6 - zAMX7|)/3 \quad (1c)$$

Note that in deriving the Z feature amount, the absolute value of the difference between the maximum value of the up-down axis acceleration in the left leg reference period and the maximum value of the up-down axis acceleration in the right leg reference period adjacent to that left leg reference period may be normalized using a representative value of the up-down axis acceleration in that left leg reference period and a representative value of the up-down axis acceleration in the right leg reference period adjacent thereto. In this case, the normalized value may be used as the Z feature amount thereafter. By doing so, an increase in the estimation accuracy can be expected. Amounts such as a maximum value, a minimum value, an arithmetic average of the maximum value and the minimum value, a magnitude of an offset of the minimum value and the maximum value, or the like of the up-down axis acceleration in each reference period can be used as the representative value of the up-down axis acceleration, and the amount is not limited thereto.

Next, in step S45, the control unit 110 calculates an amount (the Y feature amount) indicating a degree of a difference between the swaying of the body (primarily the waist area) in the left-right axis direction in the left leg reference period and the swaying of the body (primarily the waist area) in the left-right axis direction in the right leg reference period, using the four steps' worth of left-right axis trajectory time-series data.

Specifically, in step S45, the control unit 110 calculates an absolute value of a difference between an absolute value of the maximum displacement in a left-right axis trajectory in a given left leg reference period contained in the four step's worth of left-right axis trajectory time-series data (for example, an even-numbered reference period) and an absolute value of the maximum displacement in the left-right axis trajectory in a right leg reference period adjacent to that left leg reference period (an odd-numbered reference period), and takes the calculated absolute value as the Y feature amount. For example, referring to FIG. 10, assuming a left-right axis maximum displacement in the reference period Stepi (where i is 4 to 7) is represented by YTMXi, the Y feature amount is an amount indicated as follows:

$$Y \text{ feature amount} = \| YTMX6 | - | YTMX7 \| \quad (2a)$$

Or:

$$Y \text{ feature amount} = \| YTMX5 | - | YTMX6 \| \quad (2b)$$

Note that the maximum displacement referred to here indicates a left-right axis coordinate value at a point in time in a single reference period further from the center axis of the travel direction, and it is assumed that the direction of the displacement does not matter.

Note that the control unit 110 may find a plurality of absolute values of the difference between the absolute value of the left-right axis maximum displacement in the left leg reference period and the absolute value of the left-right axis maximum displacement in the right leg reference period adjacent to that left leg reference period for the four step's worth of left-right axis trajectory time-series data, and may use an average value of the plurality of the absolute values of the differences found in this manner as the Y feature amount. In this case, referring to FIG. 10, the following may by employed:

$$Y \text{ feature amount} = (\| YTMX4 | - | YTMX5 \| + \| YTMX5 | - | YTMX6 \| + \| TTMX6 | - | ZAMX7 \|)/3 \quad (2c)$$

Or:

$$Y \text{ feature amount} = (\| YTMX4 | - | YTMX5 \| + \| TTMX6 | - | ZAMX7 \|)/2 \quad (2d)$$

Note that in deriving the Y feature amount as well, the absolute value of the difference between the absolute value of the left-right axis maximum displacement in the left leg reference period and the absolute value of the left-right axis maximum displacement in the right leg reference period adjacent to that left leg reference period may be normalized using a representative value of the left-right axis trajectory in that left leg reference period and a representative value of the left-right axis trajectory in the right leg reference period adjacent thereto. In this case, the normalized value may be used as the Y feature amount thereafter. By doing so, an increase in the estimation accuracy can be expected. Amounts such as a maximum value, a minimum value, an arithmetic average of the maximum value and the minimum value, a magnitude of an offset of the minimum value and the maximum value, or the like of the left-right axis trajectory in each reference period can be used as the representative value of the left-right axis trajectory, and the amount is not limited thereto.

Next, in step S46, the control unit 110 calculates an amount (the X feature amount) indicating a degree of a difference between the swaying of the body (primarily the waist area) in the front-rear axis direction in the left leg reference period and the swaying of the body (primarily the waist area) in the front-rear axis direction in the right leg reference period, using the four steps' worth of front-rear axis acceleration time-series data.

Specifically, in step S46, the control unit 110 calculates an absolute value of a difference between a maximum value of the front-rear axis acceleration in a given left leg reference period contained in the four step's worth of front-rear axis acceleration time-series data (for example, an even-numbered reference period) and a maximum value of the front-rear axis acceleration in a right-leg reference period (an odd-numbered reference period) adjacent to the stated left-leg reference period, and takes the calculated absolute value as the X feature amount. For example, referring to FIG. 11, assuming a front-rear axis acceleration maximum value in the reference period Stepi (where i is 4 to 7) is represented by XAMXi, the X feature amount is an amount indicated as follows:

$$X \text{ feature amount} = |XAMX6 - XAMX7| \quad (3a)$$

Or:

$$X \text{ feature amount} = |XAMX5 - XAMX6| \quad (3b)$$

Note that the control unit 110 may find a plurality of absolute values of the difference between the maximum value of the front-rear axis acceleration in the left leg reference period and the maximum value of the front-rear axis acceleration in the right leg reference period adjacent to that left leg reference period for the four step's worth of front-rear axis acceleration time-series data, and may use an average value of the plurality of the absolute values of the differences found in this manner as the X feature amount. In this case, referring to FIG. 11, $$X \text{ feature amount} = (|XAMX4 - XAMX5| + |XAMX5 - XAMX6| + |XAMX6 - XAMX7|)/3 \quad (3c)$$

Note that in deriving the X feature amount as well, the absolute value of the difference between the maximum value of the front-rear axis acceleration in the left leg reference period and the maximum value of the front-rear axis acceleration in the right leg reference period adjacent to that left leg reference period may be normalized using a representative value of the front-rear axis acceleration in that left leg reference period and a representative value of the front-rear axis acceleration in the right leg reference period adjacent thereto. In this case, the normalized value may be used as the X feature amount thereafter. By doing so, an increase in the estimation accuracy can be expected. Amounts such as a maximum value, a minimum value, an arithmetic average of the maximum value and the minimum value, a magnitude of an offset of the minimum value and the maximum value, or the like of the front-rear axis acceleration in each reference period can be used as the representative value of the front-rear axis acceleration, and the amount is not limited thereto.

In this manner, operating as the computation unit, the control unit 110 calculates the Z feature amount indicating a degree of a difference between the swaying of the body (primarily the waist area) in the up-down axis direction in the left leg reference period and the swaying of the body (primarily the waist area) in the up-down axis direction in the right leg reference period, using the up-down axis acceleration time-series data, derives the left-right axis trajectory time-series data from the left-right axis acceleration time-series data, calculates the Y feature amount indicating a degree of symmetry between the swaying of the body (primarily the waist area) in the left-right axis direction in the left leg reference period and the swaying of the body (primarily the waist area) in the left-right axis direction in the right leg reference period, from the derived left-right axis trajectory time-series data, and calculates the X feature amount, which is an amount indicating a degree of a difference between the swaying of the body (primarily the waist area) in the front-rear axis direction in the left leg reference period and the swaying of the body (primarily the waist area) in the front-rear axis direction in the right leg reference period, from the front-rear axis acceleration time-series data.

Referring to FIG. 12, in step S5, the control unit 110 operates as the evaluation unit, and evaluates the left-right balance of the measurement subject during walking from a plurality of standpoints (a left-right difference in the swaying of the body in the up-down axis direction, a left-right difference in the swaying of the body in the left-right axis direction, and a left-right difference in the swaying of the body in the front-rear axis direction).

A specific method for evaluation will be described with reference to FIG. 14. FIG. 14 is a table that consolidates results of evaluating the left-right balance for a plurality of measurement subjects (person A to person E). A sub-table SCY indicates results of a multi-stage evaluation of the left-right balance in the left-right axis direction carried out over 11 stages, a sub-table SCZ indicates results of a multi-stage evaluation of the left-right balance in the up-down axis direction carried out over 11 stages, and a sub-table SCX indicates results of a multi-stage evaluation of the left-right balance in the front-rear axis direction carried out over 11 stages. A sub-table CMT is an example of comments added to the evaluation results for each measurement subject and provided to users.

According to the Z feature amount, the Y feature amount, and the X feature amount used in the present specification, the magnitudes of the feature amounts of those axes increase as the left-right differences in the swaying in the respective three axis directions increase for the measurement subject, as is clear from the definitions and so on of those feature amounts (Formulas (1a) to (3c)).

Accordingly, in step S5 (FIG. 12), the control unit 110 compares the Z feature amount with a predetermined reference value (a first reference value), and makes an evaluation indicating that there is a left-right difference in the swaying of the body (primarily the waist area) in the up-down direction in the case where the Z feature amount is greater than the first reference value. Note that the first reference value is an experimental value found by observing a plurality of measurement subjects. Conversely, in the case where the Z feature amount is less than or equal to the first reference value, an evaluation is made indicating that there is no left-right difference in the swaying of the body (primarily the waist area) in the up-down direction.

Furthermore, by providing one or more sub-references from zero to the first reference value, the control unit 110 further evaluates the left-right balance over multiple stages in the case where an evaluation has been made indicating that there is no left-right difference in the up-down movement of the body (primarily the waist area), and by providing one or more sub-references in a value range greater than the first reference value, control unit 110 further evaluates the left-right balance over multiple stages in the case where an evaluation has been made indicating that there is a left-right difference in the up-down movement of the body (primarily the waist area).

In the example illustrated in FIG. 14, values of 0, 1, and 2 for an evaluation unit "skew" correspond to a case of an evaluation indicating that there is no left-right difference in the up-down movement (a case where the Z feature amount is less than or equal to the first reference value), whereas a value of 3 or more for the evaluation unit "skew" corresponds to a case of an evaluation indicating that there is a left-right difference in the up-down movement (a case where the Z feature amount is greater than the first reference value).

In addition, in step S5 (FIG. 12), the control unit 110 compares the Y feature amount with a predetermined reference value (a second reference value), and makes an evaluation indicating that there is a left-right difference in the swaying of the body (primarily the waist area) in the left-right direction in the case where the Y feature amount is greater than the second reference value. Note that the second reference value is an experimental value found by observing a plurality of measurement subjects. Conversely, in the case where the Y feature amount is less than or equal to the second reference value, an evaluation is made indicating that there is no left-right difference in the swaying of the body (primarily the waist area) in the left-right direction.

Furthermore, by providing one or more sub-references from zero to the second reference value, the control unit 110 further evaluates the left-right balance over multiple stages in the case where an evaluation has been made indicating that there is no left-right difference in the swaying in the left-right direction of the body (primarily the waist area), and by providing one or more sub-references in a value range greater than the second reference value, control unit 110 further evaluates the left-right balance over multiple stages in the case where an evaluation has been made indicating that there is a left-right difference in the swaying in the left-right direction of the body (primarily the waist area).

In the example illustrated in FIG. 14, values of 0, 1, and 2 for the evaluation unit "skew" correspond to a case of an evaluation indicating that there is no left-right difference in the swaying in the left-right direction (a case where the Y feature amount is less than or equal to the second reference value), whereas a value of 3 or more for the evaluation unit "skew" corresponds to a case of an evaluation indicating that there is a left-right difference in the swaying in the left-right direction (a case where the Y feature amount is greater than the second reference value).

In addition, in step S5 (FIG. 12), the control unit 110 likewise compares the X feature amount with a predetermined reference value (a third reference value), and makes an evaluation indicating that there is a left-right difference in the swaying of the body (primarily the waist area) in the front-rear direction in the case where the X feature amount is greater than the third reference value. Note that the third reference value is also an experimental value found by observing a plurality of measurement subjects. Conversely, in the case where the X feature amount is less than or equal to the third reference value, an evaluation is made indicating that there is no left-right difference in the swaying of the body (primarily the waist area) in the front-rear direction.

Furthermore, by providing one or more sub-references from zero to the third reference value, the control unit 110 further evaluates the left-right balance over multiple stages in the case where an evaluation has been made indicating that there is no left-right difference in the swaying in the front-rear direction of the body (primarily the waist area), and by providing one or more sub-references in a value range greater than the third reference value, control unit 110 further evaluates the left-right balance over multiple stages in the case where an evaluation has been made indicating that there is a left-right difference in the swaying in the front-rear direction of the body (primarily the waist area).

In the example illustrated in FIG. 14, values of 0, 1, and 2 for the evaluation unit "skew" correspond to a case of an evaluation indicating that there is no left-right difference in the swaying in the front-rear direction (a case where the X feature amount is less than or equal to the third reference value), whereas a value of 3 or more for the evaluation unit "skew" corresponds to a case of an evaluation indicating that there is a left-right difference in the swaying in the front-rear direction (a case where the X feature amount is greater than the third reference value).

Finally, in step S6, the control unit 110 makes an overall evaluation of the left-right balance of the measurement subject's gait posture based on the Z feature amount, the Y feature amount, and the X feature amount. Here, the control unit 110 makes an evaluation that there is no left-right difference in the measurement subject's gait posture in the case where, for the swaying of the body in each of the three axis directions, the swaying in all of the directions have been evaluated as having no left-right difference. Conversely, the control unit 110 makes an evaluation that there is a left-right difference in the measurement subject's gait posture in the case where, for the swaying of the body in each of the three axis directions, the swaying in at least one of the directions has been evaluated as having a left-right difference. The control unit 110 then outputs, to the smartphone 200, the evaluation results for the respective axes, the overall evaluation result, information specifying an axis in which a left-right difference appears from the respective axis evaluations, and so on. The control unit 110 may output messages, such as those in the sub-table CMT for comments indicated in FIG. 14, to the smartphone 200.

Upon receiving the information from the activity meter 100, the smartphone 200 displays the left-right difference evaluation results ("skew" values) for each axis, the overall evaluation result, the evaluation comments, and so on in the display unit 240. In other words, the display unit 240 operates as the notification unit for notifying the user of the evaluation results. A message reading, for example, "your gait posture shows a left-right difference in the up-down (left-right and/or front-back) swaying of your waist" is displayed in the display unit 240 of the smartphone 200. Note that a trend of the left-right balance may be displayed in the display unit 240 in an intuitive manner using an illustration, which is a still image, an animation, which is a moving picture, or the like.

Figure 15:
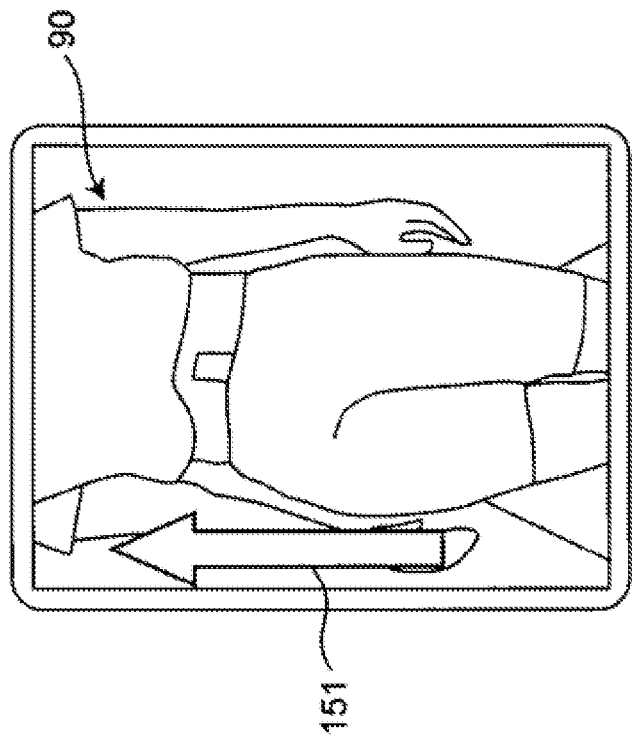
FIGS. 15A and 15B are diagrams illustrating examples of moving picture frames indicating a gait posture in which there is a left-right difference in swaying in the up-down axis direction of a person's body while walking.
Figure 15:
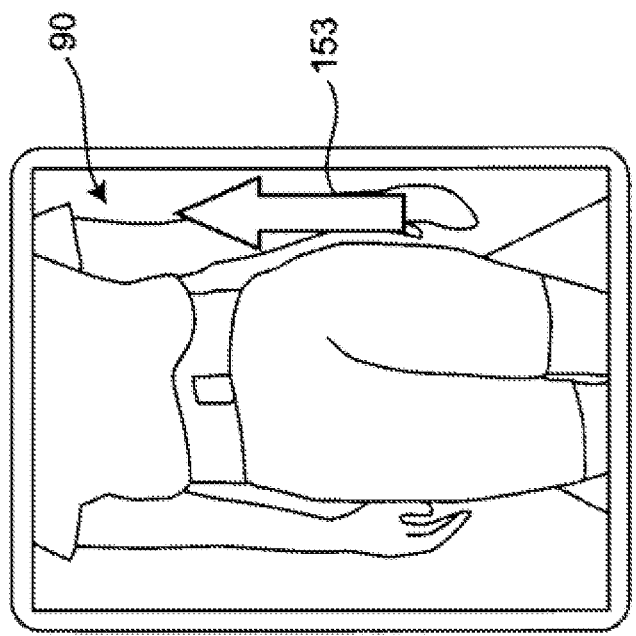

FIGS. 15A and 15B illustrate selected frames in a moving picture stored in the memory 220 (the storage unit) of the smartphone 200 and displayed in the display unit 240 (the notification unit) when the swaying of the waist in the up-down direction has been evaluated as having a left-right difference. This moving picture may be any moving picture that visually expresses the walking actions appearing in the case where the Z feature amount is greater than the first reference value. The moving picture may be a moving picture in which the difference in the swaying in the up-down direction created by the supporting leg is exaggerated more than walking actions appearing in the case where the Z feature amount is equal to the first reference value. In addition, graphics such as an arrow 151 and an arrow 153 may be added to show the user the direction of the swaying in which the left-right difference appears. Furthermore, features of the measurement subject's gait posture (the directionality of actions in which the left-right difference appears) may be shown to the user by displaying moving picture frames such as those illustrated in FIGS. 15A and 15B as still images.

Figure 16:
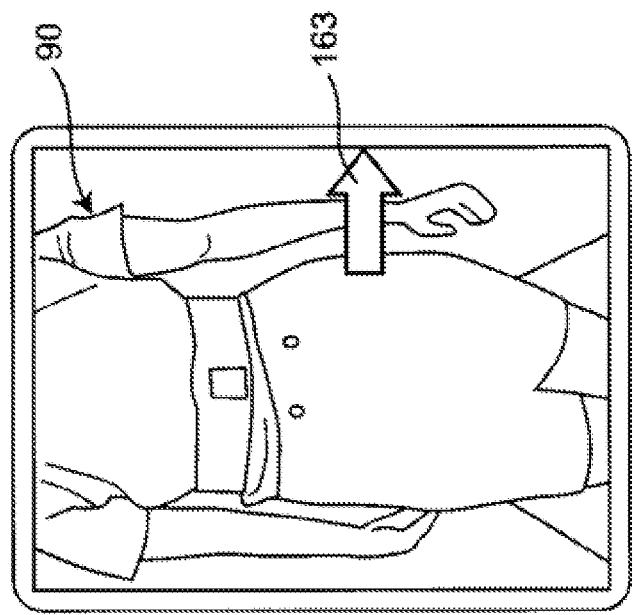
FIGS. 16A and 16B are diagrams illustrating examples of moving picture frames indicating a gait posture in which there is a left-right difference in swaying in the left-right axis direction of a person's body while walking.
Figure 16:
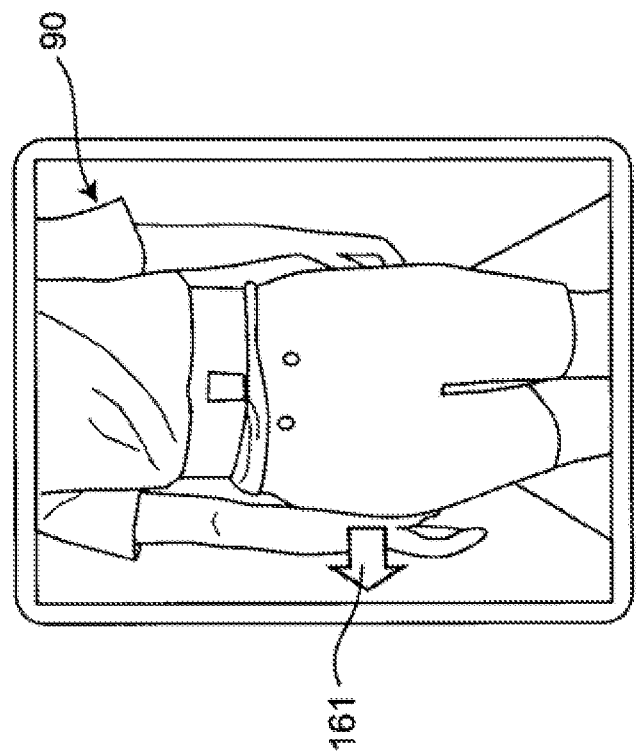

FIGS. 16A and 16B illustrate selected frames in a moving picture stored in the memory 220 (the storage unit) of the smartphone 200 and displayed in the display unit 240 (the notification unit) when the swaying of the waist in the left-right direction has been evaluated as having a left-right difference. This moving picture may be any moving picture that visually expresses the walking actions appearing in the case where the Y feature amount is greater than the second reference value. The moving picture may be a moving picture in which the difference in the swaying in the left-right direction created by the supporting leg is exaggerated more than walking actions appearing in the case where the Y feature amount is equal to the second reference value. In addition, graphics such as an arrow 161 and an arrow 163 may be added to the moving picture to show the user the direction of the swaying in which the left-right difference appears. Furthermore, features of the measurement subject's gait posture (the directionality of actions in which the left-right difference appears) may be shown to the user by displaying moving picture frames such as those illustrated in FIGS. 16A and 16B as still images.

Figure 17:
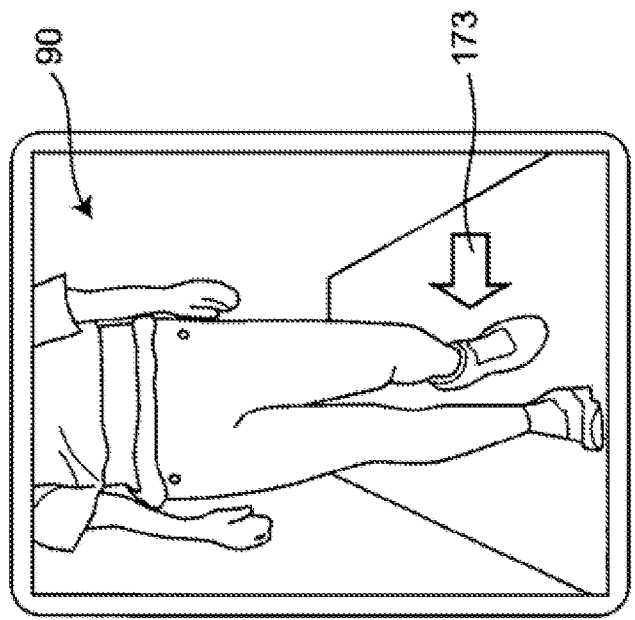
FIGS. 17A and 17B are diagrams illustrating examples of moving picture frames indicating a gait posture in which there is a left-right difference in swaying in the front-rear axis direction of a person's body while walking.
Figure 17:
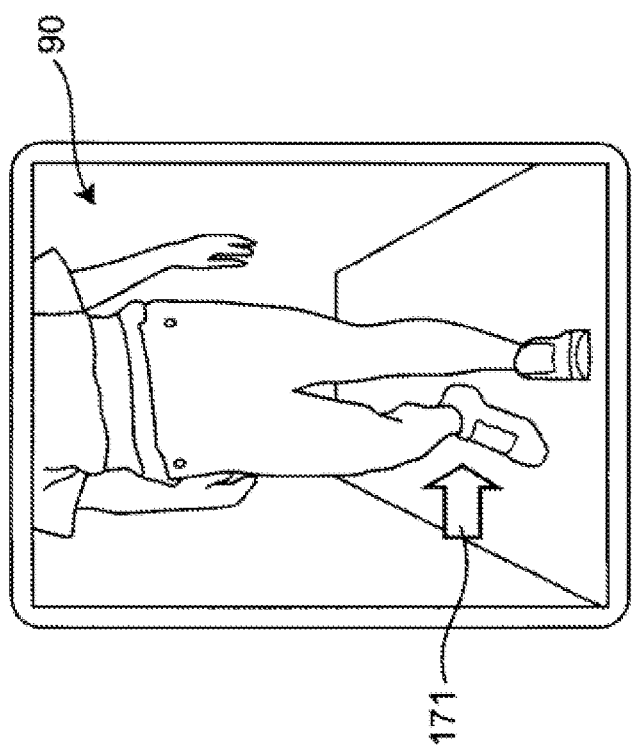

FIGS. 17A and 17B illustrate selected frames in a moving picture stored in the memory 220 (the storage unit) of the smartphone 200 and displayed in the display unit 240 (the notification unit) when the swaying of the waist in the front-rear direction has been evaluated as having a left-right difference. This moving picture may be any moving picture that visually expresses the walking actions appearing in the case where the X feature amount is greater than the third reference value. The moving picture may be a moving picture in which the difference in the swaying in the front-rear direction created by the supporting leg is exaggerated more than walking actions appearing in the case where the X feature amount is equal to the third reference value. In addition, graphics such as an arrow 171 and an arrow 173 may be added to the moving picture to show the user the direction of the swaying in which the left-right difference appears. Furthermore, features of the measurement subject's gait posture (the directionality of actions in which the left-right difference appears) may be shown to the user by displaying moving picture frames such as those illustrated in FIGS. 17A and 17B as still images.

By viewing the content displayed in the display unit 240, the user can obtain not only information indicating whether or not there is a breakdown in the left-right balance in his/her posture and actions while walking, but also information indicating what sort of visual features his/her gait posture has due to the breakdown in the left-right balance of his/her gait posture and actions. Knowing what sort of visual features his/her gait posture has is extremely useful information for the user to improve his/her gait posture and actions. Accordingly, the user can efficiently improve his/her gait posture and actions.

Although the activity meter 100 and the smartphone 200 communicate with each other through BLE communication in the aforementioned embodiment, the invention is not limited thereto. For example, the activity meter 100 and the smartphone 200 may communicate through NFC (Near Field Communication) when the smartphone 200 and the activity meter 100 are near each other.

In addition, although the gait posture meter according to the present invention is described as being configured as a system including the activity meter 100 and the smartphone 200 in the aforementioned embodiment, the invention is not limited thereto.

For example, the gait posture meter according to the present invention may be constituted by the smartphone 200 only.

Such a case assumes that the smartphone 200 includes an accelerometer. In addition, a program that causes the control unit 210 to quantitatively evaluate whether or not the gait posture of a person is a correct posture, and more specifically, a program that evaluates a left-right difference in the swaying of a body while walking, is installed in the memory 220 of the smartphone 200. Through this, the gait posture meter according to the present invention can be configured as a small-sized, compact unit.

This program can be recorded onto a recording medium such as a CD, a DVD, a flash memory, or the like as application software. By installing the application software recorded onto the recording medium in what is substantially a computer device, such as a smartphone, a personal computer, a PDA (personal digital assistant), or the like, that computer device can be caused to execute a method for quantitatively evaluating whether or not the gait posture of a person is a correct posture.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A gait posture meter that evaluates a gait posture of a measurement subject, the gait posture meter comprising:
   an accelerometer that is affixed to a centerline of a waist area of the measurement subject and that outputs an acceleration in each of an up-down axis direction, a left-right axis direction, and a front-rear axis direction; and
   a controller that calculates a Z feature amount that is a difference between a maximum value of an up-down axis acceleration of the waist area in a left leg reference period in which a body of the measurement subject is supported by a left leg and a maximum value of an up-down axis acceleration of the waist area in a right leg reference period in which the measurement subject's body is supported by a right leg using a first timewise change waveform in the up-down axis acceleration outputted by the accelerometer, calculates a Y feature amount that is a difference between a maximum displacement of a left-right axis direction trajectory of the waist area in the left leg reference period and a maximum displacement of the left-right axis direction trajectory of the waist area in the right leg reference period by finding a second-level integration of the left-right axis acceleration outputted by the accelerometer, and calculates an X feature amount that is a difference between a maximum value of a front-rear axis acceleration of the waist area in the left leg reference period and a maximum value of a front-rear axis acceleration of the waist area in the right leg reference period using a second timewise change waveform in the front-rear axis acceleration outputted by the accelerometer; wherein
   the controller evaluates the gait posture of the measurement subject based on a left-right balance from three standpoints including:
   (i) a first left-right difference in a swaying of the measurement subject's body in the up-down axis direction based on the Z feature amount,
   (ii) a second left-right difference in the swaying of the measurement subject's body in the left-right axis direction based on the Y feature amount, and
   (iii) a third left-right difference in the swaying of the measurement subject's body in the front-rear axis direction based on the X feature amount.

2. The gait posture meter according to claim 1, wherein
   the controller compares the Z feature amount to a pre-set first reference and evaluates, in stages, the first left-right difference;
   the controller compares the Y feature amount to a pre-set second reference and evaluates, in stages, the second left-right difference; and
   the controller compares the X feature amount to a pre-set third reference and evaluates, in stages, the third left-right difference.

3. The gait posture meter according to claim 2, further comprising:
   a display that displays results of the evaluations carried out by the controller.

4. The gait posture meter according to claim 3, further comprising:
   a storage that stores a first still image or moving picture indicating a gait posture in which the first left-right difference of the swaying in the up-down axis direction caused by the disparity in the supporting legs is greater than the first reference, a second still image or moving picture indicating a gait posture in which the second left-right difference of the swaying in the left-right axis direction caused by the disparity in the supporting legs is greater than the second reference, and a third still image or moving picture indicating a gait posture in which the third left-right difference of the swaying in the front-rear axis direction caused by the disparity in the supporting legs is greater than the third reference,
   wherein the display makes a notification that the first left-right difference in the up-down swaying of the waist area is high using the first still image or moving picture in the case where the controller evaluates the first left-right difference as being greater than the first reference, makes a notification that the second left-right difference in the left-right swaying of the waist area is high using the second still image or moving picture in the case where the controller evaluates the second left-right difference as being greater than the second reference, and makes a notification that the third left-right difference in the front-back swaying of the waist area is high using the third still image or moving picture in the case where the controller evaluates the third left-right difference as being greater than the third reference.

5. The gait posture meter according to claim 4,
wherein the first still image or moving picture stored in the storage includes an image of the gait posture that exaggerates the first left-right difference of the up-down swaying of the waist area more than the gait posture in the case where the first left-right difference is the same as the first reference;
the second still image or moving picture stored in the storage includes an image of the gait posture that exaggerates the second left-right difference of the left-right swaying of the waist area more than the gait posture in the case where the second left-right difference is the same as the second reference; and
the third still image or moving picture stored in the storage includes an image of the gait posture that exaggerates the third left-right difference of the front-back swaying of the waist area more than the actual gait posture in the case where the third left-right difference is the same as the third reference.

6. The gait posture meter according to claim 1,
wherein for each of four or more sequential left leg reference periods and right leg reference periods that appear in an alternating manner, the controller finds the difference between the maximum value of the up-down axis acceleration in the left leg reference period and the maximum value of the up-down axis acceleration in the right leg reference period adjacent to the stated left leg reference period and then finds the Z feature amount using an average value of the plurality of the differences that have been found, finds the difference between the maximum displacement of the left-right axis direction trajectory in the left leg reference period and the maximum displacement of the left-right axis direction trajectory in the right leg reference period adjacent to the stated left leg reference period and then finds the Y feature amount using an average value of the plurality of the differences that have been found, and finds the difference between the maximum value of the front-rear axis acceleration in the left leg reference period and the maximum value of the front-rear axis acceleration in the right leg reference period adjacent to the stated left leg reference period and then finds the X feature amount using an average value of the plurality of the differences that have been found.

7. The gait posture meter according to claim 2,
wherein the controller evaluates the first left-right difference in the up-down swaying of the waist area over three or more stages using, in addition to the first reference, a plurality of pre-set first sub-references that are different from the first reference, evaluates the second left-right difference in the left-right swaying of the waist area over three or more stages using, in addition to the second reference, a plurality of pre-set second sub-references that are different from the second reference, and evaluates the third left-right difference in the front-back swaying of the waist area over three or more stages using, in addition to the third reference, a plurality of pre-set third sub-references that are different from the third reference.

8. The gait posture meter according to claim 2,
wherein the controller evaluates the gait posture of the measurement subject as not having a left-right difference in the case where the first left-right difference is less than or equal to the first reference, the second left-right difference is less than or equal to the second reference, and the third left-right difference is less than or equal to the third reference; and
the controller evaluates the gait posture of the measurement subject as having a left-right difference in the case where the first left-right difference is greater than the first reference, the second left-right difference is greater than the second reference, or the third left-right difference is greater than the third reference.

9. A non-transitory computer readable medium including a program for causing a computer to execute a method for evaluating a gait posture of a measurement subject, the method comprising:
a step of obtaining an output of an acceleration in each of an up-down axis direction, a left-right axis direction, and a front-rear axis direction from an accelerometer that is affixed to a centerline of a waist area of the measurement subject;
a step of calculating a Z feature that is a difference between a maximum value of an up-down axis acceleration of the waist area in a left leg reference period in which a body of the measurement subject is supported by a left leg and a maximum value of an up-down axis acceleration of the waist area in a right leg reference period in which the measurement subject's body is supported by a right leg using a first timewise change waveform in the up-down axis acceleration outputted by the accelerometer, calculating a Y feature amount that is a difference between a maximum displacement of a left-right axis direction trajectory of the waist area in the left leg reference period and a maximum displacement of the left-right axis direction trajectory of the waist area in the right leg reference period by finding a second-level integration of the left-right axis acceleration outputted by the accelerometer, and calculating an X feature amount that is a difference between a maximum value of a front-rear axis acceleration of the waist area in the left leg reference period and a maximum value of a front-rear axis acceleration of the waist area in the right leg reference period using a second timewise change waveform in the front-rear axis acceleration outputted by the accelerometer; and
a step of evaluating the gait posture of the measurement subject based on a left-right balance from three standpoints including:
(i) a first left-right difference in a swaying of the measurement subject's body in the up-down axis direction based on the Z feature amount,
(ii) a second left-right difference in the swaying of the measurement subject's body in the left-right axis direction based on the Y feature amount, and
(iii) a third left-right difference in the swaying of the measurement subject's body in the front-rear axis direction based on the X feature amount.

* * * * *